(12) United States Patent
Greene et al.

(10) Patent No.: US 6,468,754 B1
(45) Date of Patent: Oct. 22, 2002

(54) VECTOR AND METHOD FOR TARGETED REPLACEMENT AND DISRUPTION OF AN INTEGRATED DNA SEQUENCE

(75) Inventors: Amy L. Greene, Sunnyvale; Hua Zhou, Santa Clara; Silke Thode, Los Gatos; Kurt Jarnigan, San Mateo, all of CA (US)

(73) Assignee: Iconix Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 09/837,863

(22) Filed: Apr. 17, 2001

Related U.S. Application Data
(60) Provisional application No. 60/198,498, filed on Apr. 18, 2000.

(51) Int. Cl.[7] .................. C12N 15/85; C12N 15/87; C12Q 1/68
(52) U.S. Cl. .................. 435/6; 435/320.1; 435/455; 435/465
(58) Field of Search .................. 435/320.1, 6, 455, 435/465

(56) References Cited

U.S. PATENT DOCUMENTS 6,025,192 A   2/2000  Beach et al. ............. 435/320.1

OTHER PUBLICATIONS

Masuda et al., Effects of procollagen C–proteinase enhancer protein on the growth of cultured rat fibroblasts revealed by an excisable retroviral vector, 1998, Cell Growth & Differentiation, vol. 9, pp. 381–391.*

Fukushige et al., "Genomic Targeting With a Positive–Selection lox Integration Vector Allows Highly Reproduciable Gene Expression in Mammalian Cell," *Proc. Natl. Acad. Sci. U.S.A.* 89(17):7905–7909 (1992).

O'Gorman et al., "Recombinase–Mediated Gene Activation and Site–Specific Integration in Mammalian Cells," *Science* 251:1351–1335 (1991).

Sauer et al., "Cre–Stimulated Recombination at loxP–Containing DNA Sequences Placed into the Mammalian Genome," *Nucleic Acids Research.* 17(1):147–161 (1989).

Sauer et al., "Site–Specific DNA Recombination in Mammalian Cells by the Cre Recombinase of Bacteriophage P1," *Proc. Natl. Acad. Sci. U.S.A.* 85(14):5166–5170.

Sauer et al., "Targeted Insertion of Exogenous DNA into the Eukaryotic Genome by the Cre Recombinase," *The New Biologist* 2(5):441–449 (1990).

Bouhassira et al., "Transcriptional Behavior of LCR Enhancer Elements Integrated at the Same Chromosomal Locus by Recombinase–Mediated Cassette Exchange," *Blood* 90(9):3332–3344 (1997).

Feng et al., "Site–Specific Chromosomal Integration in Mammalian Cells: Highly Efficient CRE Recombinase–Mediated Cassette Exchange," *Journal of Molecular Biology* 292(4):779–785 (1999).

Kirchoff et al., "Identification of Mammalian Cell Clones Exhibiting Highly Regulated Expression from Inducible Promoters," *Trends in Genetics* 11(6):219–220 (1995).

Metzger et al., "Conditional Site–Specific Recombination in Mammalian Cells Using a Ligand–Dependent Chimeric CRE Recombinase," *Proc. Natl. Acad. Sci. U.S.A.* 92(15):6991–6995 (1995).

Seibler et al., "Double–Reciprocal Crossover Mediated by FLP–Recombinase: A Concept and an Assay," *Biochemistry, American Chemical Society* 36(7):1740–1747 (1997).

Seibler et al., "DNA Cassette Exchange in ES Cells Mediated by FLP Recominase: An Efficient Strategy for Repeated Modification of Tagged LOCI by Marker–Free Constructs," *Biochemistry* 37:6229–6234 (1998).

Snaith et al., "Multiple Cloning Sites Carrying LOXP and FRT Recognition Sites for the CRE and FlP Site–Specific Recominases," *Gene* 166(1):173–174 (1995).

Zhang et al., "Inducible Site–Directed Recombination in Mouse Embryonic Stem Cells," *Nucleic Acids Research* 24(4):543–548 (1996).

* cited by examiner

Primary Examiner—James Ketter
Assistant Examiner—Daniel Sullivan
(74) *Attorney, Agent, or Firm*—Robins & Pasternak LLP

(57) ABSTRACT

Vectors of the invention facilitate selection of host cells having operably incorporated query genes, and substitution of the query gene with a different gene.

7 Claims, 5 Drawing Sheets

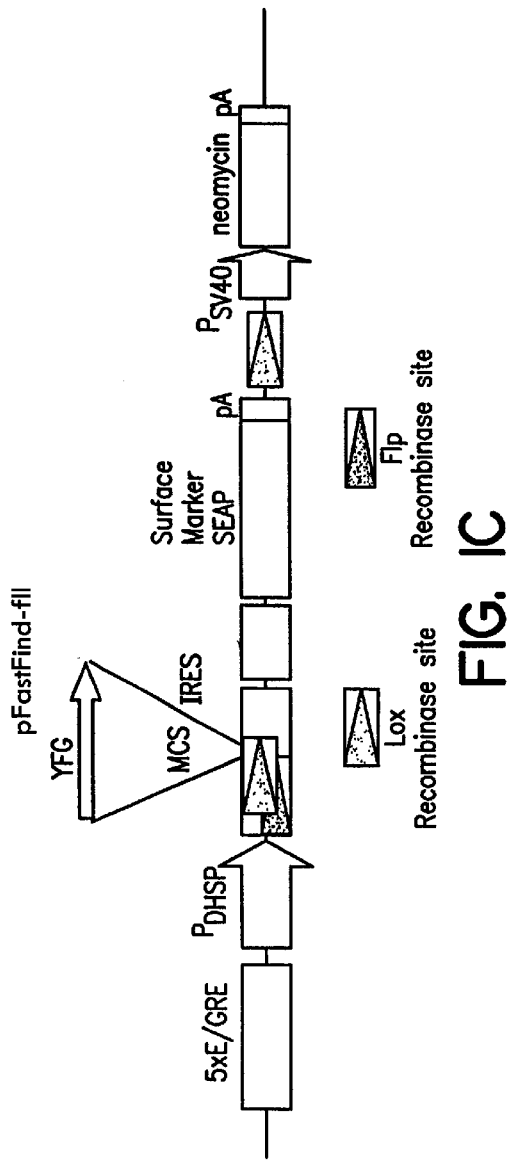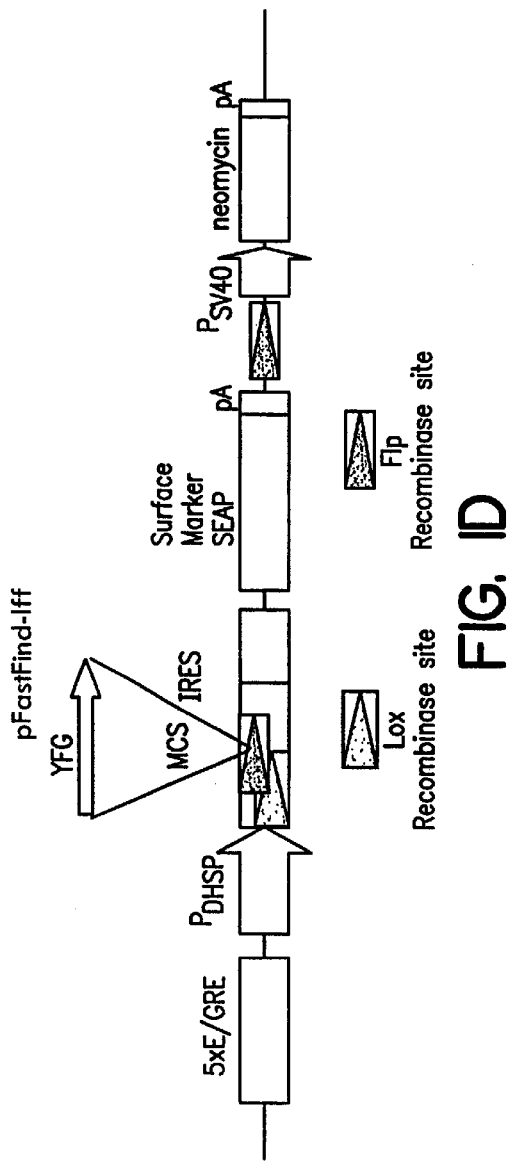

VECTOR AND METHOD FOR TARGETED REPLACEMENT AND DISRUPTION OF AN INTEGRATED DNA SEQUENCE

CROSS-REFERENCE TO RELATED APPLICATION

This application is related to provisional patent application Ser. No. 60/198,498, filed Apr. 18, 2000, from which priority is claimed under 35 USC §119(e)(1) and which is incorporated herein by reference in its entirety.

FIELD OF THE INVENTION

This invention is related generally to the fields of recombinant DNA technology and genomics. More specifically, it is related to gene targeting vectors and methods for rapidly removing or altering a DNA sequence integrated into mammalian cells or host mammalian organisms, and methods for selecting cells using the methods of the invention.

BACKGROUND OF THE INVENTION

It is possible to modify a mammalian genome by adding genetic material, but to further modify the introduced genetic material without causing additional alterations in the remaining genome has been a laborious and time consuming process. A system that would allow the simultaneous deletion of the introduced DNA and/or replacement of the introduced DNA would allow the researcher to monitor both the baseline conditions (deletion state) and any altered states of the inserted DNA in the same genetic background.

The ability to make such site specific alterations, deletions and insertions to transgenic cell lines has been described using various site specific recombinases paired with their DNA recognition sequences, such as Cre-lox or Flp-Frt (S. Fukushige et al., *Proc Natl Acad Sci USA* (1992)89(17):7905–09; S. O'Gorman, et al., *Science* (1991) 251:1351–35; B. Sauer et al., *Proc Natl Acad Sci USA* (1988) 85(14):5166–70; B. Sauer et al., *Nuc Acids Res* (1989) 17(1):147–61; B. Sauer et al., *New Biol* (1990) 2(5):441–49. However the methods employed by these workers only allowed one type of change to be made in the introduced DNA, either an insertion or a deletion. Furthermore, the methods employed by these authors to detect and characterize the recombinase formed products are very time consuming and laborious.

SUMMARY OF THE INVENTION

We have now invented a vector system and method that facilitates insertion of a query gene into a eukaryotic host cell, and the subsequent removal, insertion, and/or substitution of a different query gene and/or marker gene at the same site within the host cell. One aspect of the invention is a polynucleotide vector, comprising in order of transcription: a regulatable promoter; a first recombinase target site; a second recombinase target site different from said first recombinase target site; a cloning site suitable for insertion of a test gene; an internal ribosome binding site (IRES); an optically-active marker-encoding sequence; a third recombinase target site homologous to either said first recombinase target site or said second recombinase target site. A presently-preferred subgenus is the vector further comprising a second promoter, and a selectable marker operatively associated with said second promoter.

Another aspect of the invention is a method of selecting a host cell having a functioning test gene, comprising: providing a host cell lacking a functioning test gene; inserting into said host cell a vector, said vector comprising a regulatable promoter; a first recombinase target site; a second recombinase target site different from said first recombinase target site; a test gene; an internal ribosome binding site (IRES); a label sequence encoding a detectable marker; and a third recombinase target site homologous to either said first recombinase target site or said second recombinase target site; selecting against cells that failed to incorporate said vector; inducing said regulatable promoter; and selecting for cells that express said detectable marker. A presently preferred sub-genus is the method further comprising: contacting said host cell with a recombinase capable of catalyzing excision of said label sequence.

Another aspect of the invention is the method of altering a host cell comprising a vector of the invention, said method comprising providing a host cell comprising a vector of the invention, and contacting said cell with an effective amount of a recombinase that recognizes said first recombinase target site or said second recombinase target site, such that the portion of the vector between the recombinase target sites is deleted. A presently preferred class of the invention is the method wherein said host cell is contacted with recombinase by intracellular expression of said recombinase. Another aspect of the invention is the method of substituting a query gene and/or marker gene in a host cell, comprising providing a host cell comprising a vector of the invention, and inserting into said cell a polynucleotide comprising a recombinase target site complementary to either said first or second recombinase target site along with an effective amount of a recombinase that recognizes said recombinase target, such that the portion of the vector between the recombinase target sites is replaced with the polynucleotide portion between the two recombinase target sites.

DETAILED DESCRIPTION

Figure 1A:
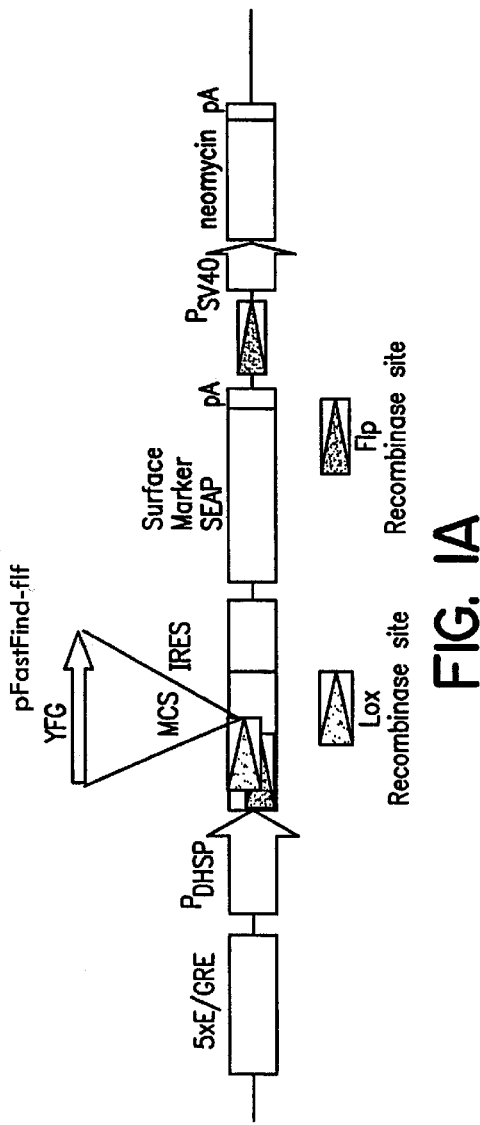
FIG. 1 is a diagram of four embodiments of the invention: the vectors pFastFindflf (A, SEQ ID NO:19), pFastFindlfl (B, SEQ ID NO:21), pFastFindffl (C, SEQ ID NO:20), and pFastFindlff (D, SEQ ID NO:22), generically referred to as "pFastFindxxx" and "pFFxxx". The vector includes an ecdysone responsive enhancer element upstream of the Heat shock protein (HSP) basal promoter. Directly downstream of the promoter are the recognition sequences for Flp recombinase and Cre recombinase, frt and loxp respectively. There is a unique PacI restriction site located distal to the loxp site. This PacI site is flanked by Vaccinia virus topoisomerase I recognition sequences (CCTTT). This site will be used to insert the query gene of interest using topo cloning or conventional methods. The IRES element creates a bicistronic message containing the query gene and the downstream optically-active marker #1. Following the optically-active marker #1 gene is a second frt or loxp site. The combination of two frt (a and d) or two loxp (b and c) sites in the same orientation allows the excision of the intervening sequences with Flp or Cre recombinase respectively. In addition to the bacterial origin of replication and the beta lactamase gene conferring ampicillin resistance in bacterial cells, this vector also contains a Neomycin resistance gene under the regulation of an SV40 promoter.

Definitions:

The terms "test gene" and "query gene" refer to a polynucleotide to be examined, whether its function is known or unknown, regardless of whether it is synthetic or identical to a known sequence.

The term "IRES" refers to an internal ribosome binding site, or other sequence capable of serving as a translational initiation point when transcribed into mRNA.

The term "optically-active marker" refers to a protein associated with the a host cell following translation. In general, marker will be a surface marker and it must be detectable either directly, by enzymatic activity, or through binding a labeled or immobilized binding partner, or by detecting the protein's intrinsic fluorescence or luminescence. The preferred embodiments will use antibody detectable surface markers. However we do not limit to surface bound antibodies.

The term "regulatable promoter" refers to a polynucleotide sequence capable of controlling the transcription of an adjacent polynucleotide, and which can be controlled by altering or adjusting the host cell's environment. The environment can be adjusted by addition or subtraction of various factors or compounds, by altering the temperature, pressure, concentration of media components, surface contact, radiation, and the like.

The term "FACS" refers to fluorescence-activated cell sorting, and includes any method for separating cells on the basis of an optically-detectable label. The label can be attached directly to the cell (for example, it can be expressed as a cell surface protein), or can be bound to the cell surface (for example, by allowing a labeled antibody to recognize and bind to a cell surface antigen). The optically detectable label can also be intracellular and (detectable using an antibody after cell permeabilization), or can be intracellular and detectable due to its intrinsic fluorescence, luminescence or by its formation of a fluorescent or luminescent product.

The term "drug marker" refers to any drug selectable marker that may be used to select for or against cells that do not retain an expressed copy of that marker gene.

The term "recombinase" refers to the class of proteins that binds a specific DNA sequence and catalyzes an exchange event between two DNA molecules containing this sequence.

A "recombinase target sequence" refers to any DNA sequence recognized by a specific recombination protein.

For example, the sequence 5'ATAACTTCGTATAATGTATGCTATACGAAGTTAT3' (SEQ ID NO:1) is an exemplary Cre recombinase target sequence.

A "protein targeting sequence" is a poly-amino acid sequence that directs cellular localization of the protein containing the sequence. For example, the HIV Tat sequence YGRKKRRQRRR (SEQ ID NO:2) directs a protein through the cell membrane.

The term "varied cloning site (VCS)" refers to a site within a cloning vector that is amenable to cloning by a number of different methods including but not limited to topocloning, TA-cloning, or standard restriction enzyme mediated cloning methods.

General Method:

We have expanded and enhanced the abilities of known cloning systems with our system of vectors (pFastFind, set forth in copending application U.S. Ser. No. 60/179,893, incorporated herein by reference). The genetic material of interest (query gene) is isolated and then placed under the regulation of an inducible promoter using various cloning strategies. This vector is then transfected into mammalian cells. Our system includes the ability to select for recombinants using both drug-selectable markers and sorting cells from this population by virtue of a cocistronic optically-active marker transcriptionally linked to the query gene. Once characterized, subsequent modifications can be made to the query gene in parallel using the two recombination systems incorporated into our vector system. The simultaneous removal and modification of the query gene enables the researcher to both validate the phenotypes associated with the query gene and alter the query gene in a time-saving manner. Finally, we have utilized a novel delivery method for the recombination protein.

A preferred embodiment of the method includes the use of surface localized optically active markers. However, we do not limit our invention to surface makers only; optically active markers can also be intracellular or in other ways cell-associated.

The first step DNA introduction vectors are designed such that the cells that successfully integrate the first vector express a different drug selection marker and optically-active epitope maker than the second vector. Thus cells that have undergone the desired site specific recombination will lose the first optically-active epitope marker and will gain a new drug selection marker and optically-active epitope marker. By employing such pairs of vectors, cells can be engineered to contain novel DNA sequences (first DNA introduction) and can then be reengineered to remove or insert a new sequence at the site of the first DNA introduction. The vectors provide for rapid execution of both step in the process by facilitating the identification and isolation of the desired cells from the first and second step of the process.

An additional important feature of both the first and second vectors is that they are designed to place the query gene and the optically-active epitope marker under control of an inducible promoter system, for example the ecdysone regulated promoter-system as set forth in the examples shown. This feature then creates both first and second DNA transgenetic cells lines in which the introduced DNA (the query gene) is under the control of exogenous chemicals; thus these vectors create cell lines in which amount of the proteins encoded by the introduced DNA can be controlled. Furthermore, since the vectors and methods label cells with regulated expression, they allow easy identification of those cells that exhibit regulated expression of a query gene (and cocistronic optically-active label) and allow for their isolation. These features reduce the time and expense of creating regulated query gene expression cells lines because they eliminate the need to isolate and expand numerous unresponsive cell clones—they allow substantial enrichment of responsive clones.

The latter feature of the vectors further enhances the ability of cell biologists and functional genomic investigators to create cell lines in which a cDNA is expressed in a regulated manner. For this purpose many types of regulons (combinations of transactivators and regulated promoters) have been invented. These include the tetracycline regulon (U. Baron et al., *Nuc Acids Res* (1995) 23(17):3605–06; H. Damke et al., *Meth Enzymol* (1995) 257:209–20; P. A. Furth et al., *Proc Natl Acad Sci USA* (1994) 91:9302–9306; M. Gossen et al., *Curr Opin Biotechnol* (1994) 5(5):516–20; M. Gossen et al., *Proc Natl Acad Sci USA* (1992) 89:5547–51; M. Gossen et al., *Biotechniques* (1995) 19(2):213–16; M. Gossen et al., *Science* (1995) 268:1766–69; M. Gossen et al., *Science* (1995) 268(5218):1766–69; K. O'Brien et al., *Gene* (1997) 184(1):115–20; F. Yao et al., *Hum Gene Ther* (1999) 10(3):419–27; F. Yao et al., *Hum Gene Ther* (1999) 10(11):1811–18; F. Yao et al., *Hum Gene Ther* (1998) 9(13):1939–50), the ecdysone regulon (D. No et al., *Proc Natl Acad Sci USA* (1996) 93(8):3346–51; K. O'Brien, supra; E. Saez et al., *Curr Opin Biotechnol* (1997) 8(5):608–16), regulons controlled by hybrid progesterone receptors (Y. Wang et al., *Proc Natl Acad Sci USA* (1994) 91(17):8180–84; Y. Wang et al., *Adv Pharmacol* (2000) 47:343–55), regulons controlled by a transplanted *E. coli* Lac/Lac repressor system (A. Fieck et al., *Nuc Acids Res* (1992) 20(7): 1785–91; D. L. Wyborski et al., *Environ Mol Mutagen* (1996) 28(4):447–58; D. L. Wyborski et al., *Mutat Res* (1995) 334(2):161–65; D. L. Wyborski et al., *Nuc Acids Res* (1991) 19(17):4647–53), the heat shock regulon, and the metalothionine regulon (reviewed in T. Clackson, *Curr Opin Chem Biol* (1997) 1(2):210–18; D. M. Harvey et al., *Curr Opin Chem Biol* (1998) 2(4):512–18; G. T. Yarranton, *Curr Opin Biotechnol* (1992) 3(5):506–11). These systems provide, with similar effort for each, clonal cell lines in which the cDNA is regulated by application of an exogenous stimulator: tetracycline, ecdysone, isopropylthiogalactopyranoside (IPTG), heat or heavy metals, respectively. The time and expense of creating these cells lines arises from the need to isolate and expand numerous randomly selected single cell clones and analyze each clone for appropriate regulation of the query gene. The cocistronic optically-active markers allow rapid isolation of the desired cell lines by use of various cell sorting and isolation methods.

Finally, methods for the manipulation of genetic information inside eukaryotic cells. all require short-term delivery of a site specific recombinase enzyme, Flp or Cre for example. This short term delivery of the recombinase enzyme as been accomplished by transient transfection of various types of recombinase expression (S. Fukushige et al., *Proc Natl Acad Sci USA* (1992) 89(17):7905–09; S. O'Gorman et al., *Science* (1991) 251(4999):1351–55; B. Sauer et al., supra). Some of the methods described here for inserting replacement genes at a recombinase target site create genomic products that will have paired recombinase target sequences. Paired recombinase target sequences allow the possible deletional rearrangement of the genetic locus. Since in this instance deletion represents an undesired reaction, it would be desirable to deliver the recombinase in a very short bolus fashion. Direct delivery of the protein to cells may provide such route, by providing a sharper bolus than transfected plasmids. Direct delivery into cells has been described for several different proteins (H. Nagahara et al., *Nat Med* (1998) 4(12):1449–52; S. R. Schwarze et al., *Trends Pharmacol Sci* (2000) 21(2):45–48; S. R. Schwarze et al., *Science* (1999) 285(5433):1569–72). Here we show the use of these methods to create a fusion protein of Flp or Cre recombinase to an appropriate sequence, causes Flp or Cre to penetrate cells and thus allows the direct use of these fusion proteins for the creation of the desired engineered cell lines.

The vectors of the invention are used as part of a two-step process. First, the vectors of the invention and their method of use allow rapid isolation of eukaryotic cell clones in which a query gene is regulated by exogenous application of an appropriate stimulus. The vector is arranged such that the query gene can be cloned immediately downstream of a regulated promoter by means of a varied cloning site (VCS). Downstream of the varied cloning site is an internal ribosome entry site (IRES), followed by a cell associated optically-active protein for which an epitope recognized by a convenient technique is available (a surrogate optically-active marker). Thus, since the optically-active epitope is co-cistronic with the query gene, both the query gene and the optically-active epitope are elevated in response to the exogenous stimulator.

The use of a surrogate optically-active marker for the query gene allows isolation of clonal cell lines with stimulator-induced expression by means of flow cytometry, magnetic cell sorting, cell panning, cell enrichment by column chromatography, by use of calorimetric cell overlay methods, and other cell enrichment techniques. The use of a surrogate optically-active marker for the query gene circumvents the need for a specific antibody to the query gene's encoded protein and circumvents any need for a biochemical assay for the query gene product. The surrogate optically-active marker allows rapid reconfirmation of the regulation and expression of the query gene by use of the above mentioned techniques.

Suitable surrogate optically-active markers include, without limitation, placental alkaline phosphatase (SEAP), β-lactamase, β2-microglobulin, green fluorescent protein and other fluorescent proteins and the like. If desired, one can select or construct any distinct optically-active protein, and prepare antibodies capable of recognizing the protein by conventional methods. The polynucleotide encoding the optically-active marker preferably further includes a secretion signal sequence (or other sequence that provides for export of the protein to the outer optically-active of the cell), and a transmembrane anchor (or other sequence that insures that the protein will remain associated with the cell optically-active). The optically-active marker is preferably relatively non-toxic to the cell and is preferably biochemically inert. The optically-active marker can exhibit enzymatic activity, which can be used as a label (for example, alkaline phosphatase, β-galactosidase, and the like), or can have rely solely on optical detection or binding (for example, as an epitope or ligand-binding partner), or can include both enzymatic and optical detection or ligand-binding features.

The presence of a optically-active marker permits one to quickly separate host cells that express the test gene (and thus the optically-active marker) from those that do not. Such separation can be effected by means of FACS (fluorescence-activated cell sorting), affinity panning, affinity column separation, and the like. Thus, one can identify host cells that express the test gene without the need to identify another phenotype or altered characteristic that results from the test gene expression. An additional feature of this system is the ability to select for cells with regulated expression of the optically-active marker and test gene.

Initially, cells that do not express the optically-active marker when the promoter is repressed or not induced would be selected, then from this pool, cells that express the marker following induction of the promoter would be selected. These cells can also be removed by using an antibody specific for the optically-active marker in combination with complement. It is also possible to perform the selection steps in reverse order, or to repeat the steps several times, although one may need to wait a sufficient period of time for the marker present on the host cell optically-active to be cleared. Additionally, one can select several different pools of cells by using different methods for inducing the promoters, for example, where the vector is cloned into position adjacent to a plurality of different promoters, or next to promoters randomly. For example, one can select a pool of cells that do not express the optically-active marker constitutively, and from this pool select a subset of cells that express the optically-active marker in response to a change in temperature. The cells that were not selected can be subjected to other conditions, for example the presence or absence of a nutrient, and any cells that respond to such conditions are then selected.

The second step of the process is applied once suitable cell clones or pools have been identified and isolated by FACS or other means. In this case, it is desirable to be able to remove the query gene or replace the query gene with another gene, an active site mutant or another query gene isoform, for example. The second step uses the vectors of the invention to allow the cells (as pools or clones) to be altered in at least two different manners using a recombinase. In this second step, an appropriate recombinase protein is provided to the cell transiently, either by transient transfection or infection with a vector encoding the recombinase or by transient provision of a form of the recombinase protein that also encodes a direct protein transfection sequence (PTD), the HIV-tat protein transfection sequence, for example. Excision of the query gene can be accomplished because of the provision in the vectors of a pair of directly repeated recombinase sequences; this allow excision of the query gene and rapid identification and isolation of the query gene deleted derivative cell line by virtue of the loss of the cocistronic optically-active marker #1. Replacement of the query gene can be accomplished because of the provision in the vectors of a single recombinase site, different from the paired sites set forth above. This site allows substitution of the query gene with another query gene. It also causes simultaneous removal of the cocistronic optically-active marker from the influence of the promoter elements, and simultaneously places a new optically-active marker and new drug selection marker into the recipient cell line. In this second use, the cell line is also provided with a second vector containing a single recombinase sequence operatively associated with the new query gene (as depicted in FIG. 2), the new optically-active marker #2, and a new drug selection marker.

Figure 1B:
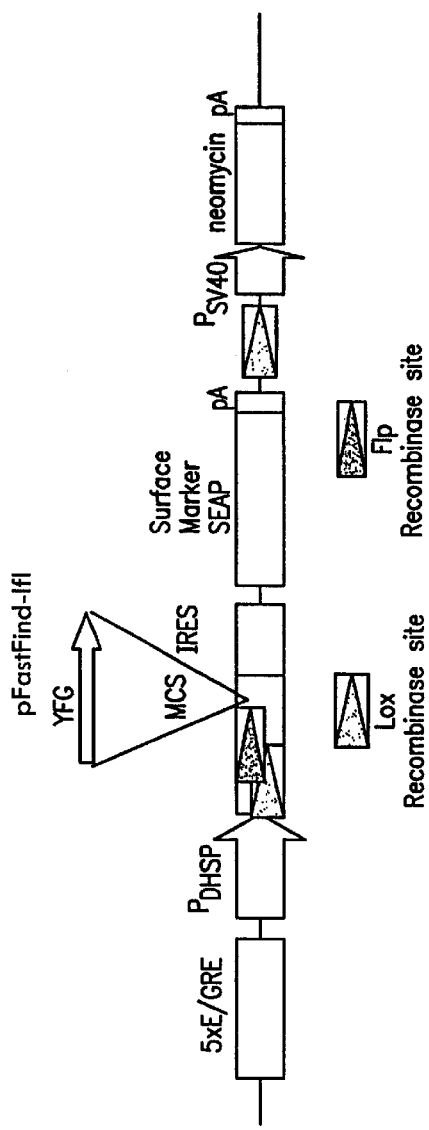
Figure 2C:
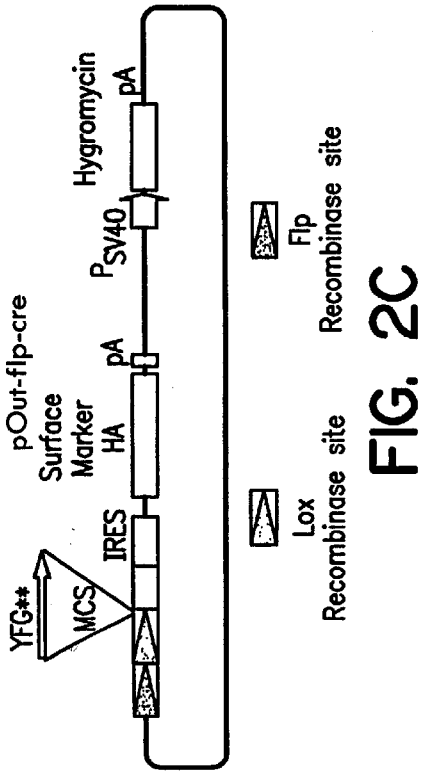
FIG. 2 is a diagram of another embodiment of the invention: the vectors pOut-flp (SEQ ID NO:25), pOut-cre (SEQ ID NO:26), pOut-flp-cre and pOut-cre-flp, generically "pOut-x"). This vector is similar to the pFastFindxxx vectors with four alterations. First, the optically-active marker #1 has been replaced with a different optically-active marker (#2) that is tran-scriptionally linked to the query gene placed in the cloning site. Second, the neomycin drug resistance gene has been replaced with the hygromycin drug resistance gene. Third, no frt or lox site is located downstream of the optically-active marker. Finally, this vector does not contain an ecdysone inducible enhancer element or promoter.
Figure 2D:
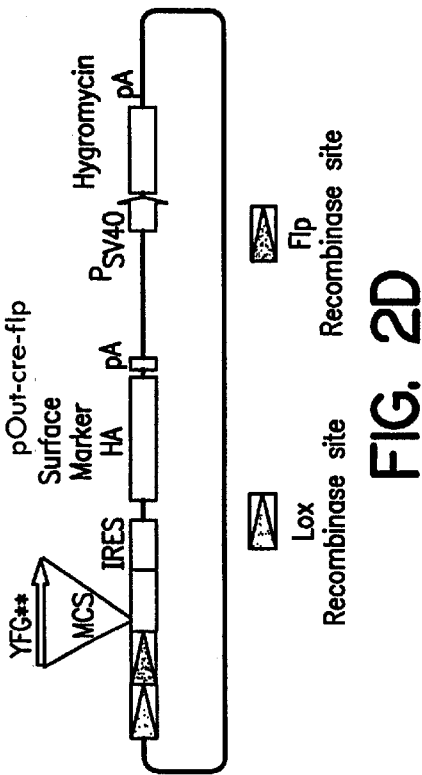
Figure 2A:
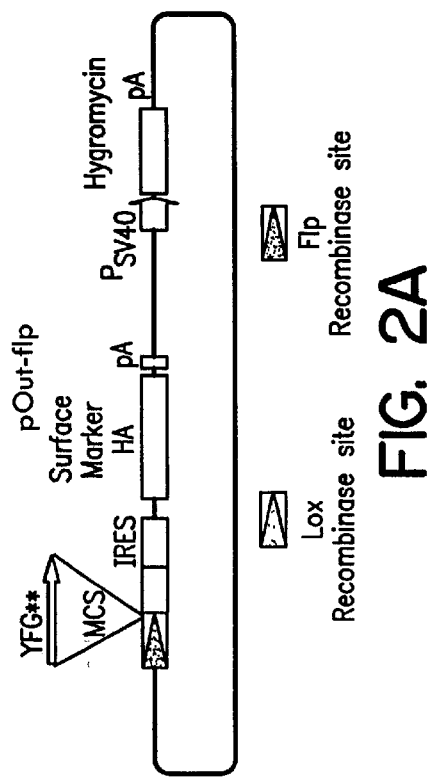
Figure 2B:
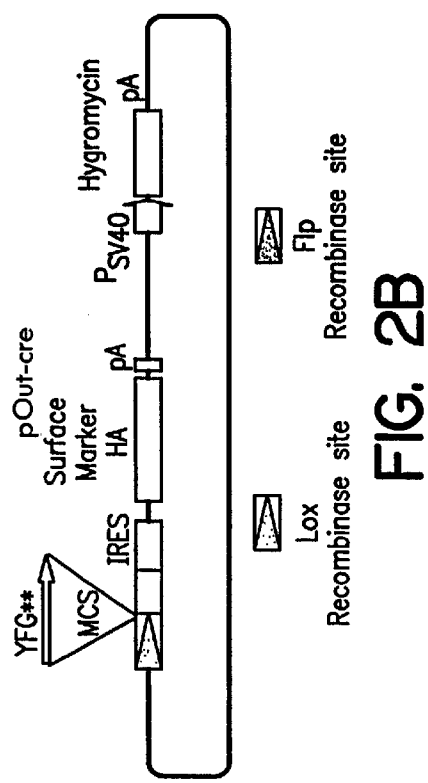
Figure 3:
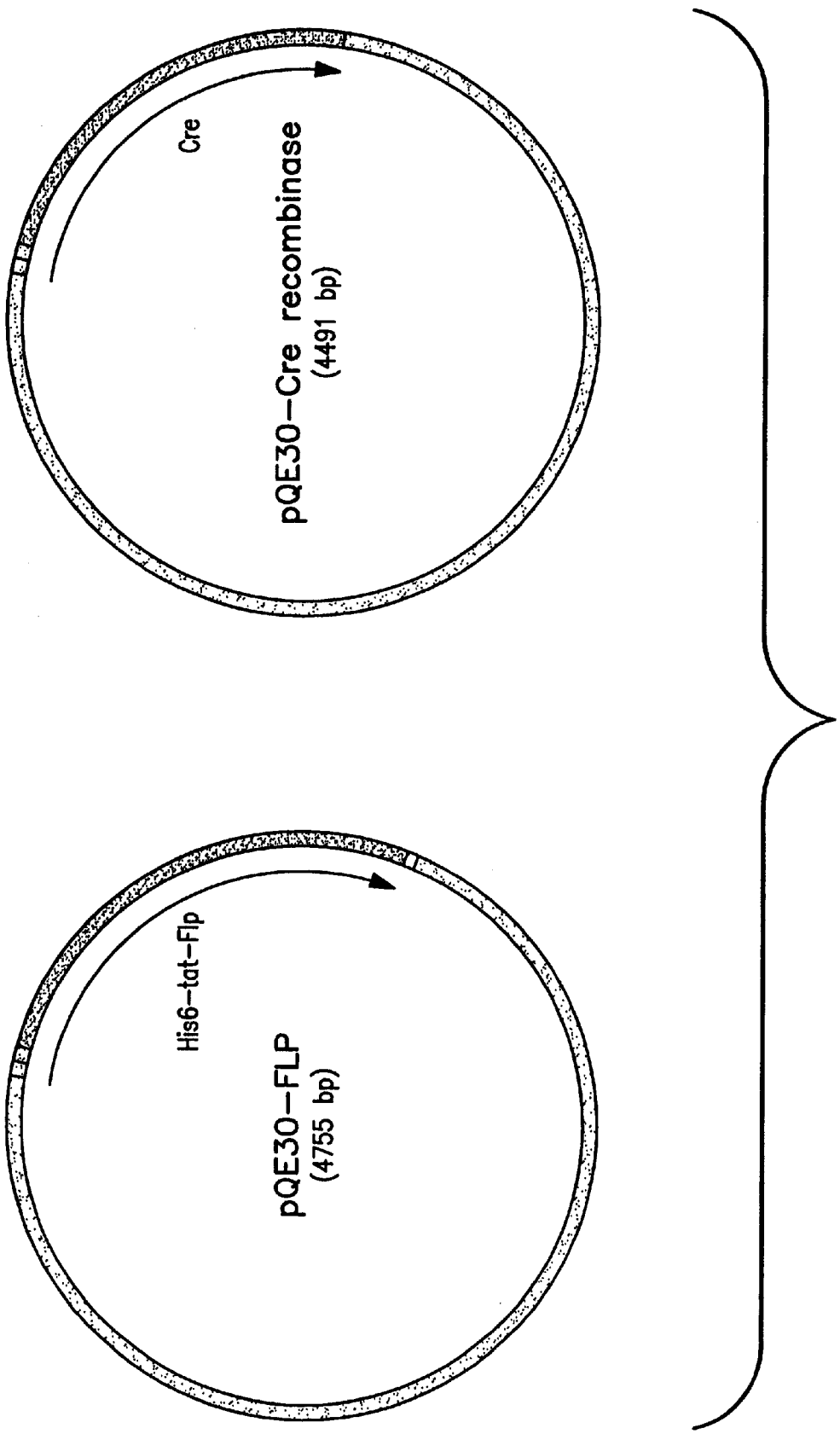
FIG. 3 is a diagram of another embodiment of the invention: the vectors pQE30-Cre (SEQ ID NO:23) and pQE30-Flp (SEQ ID NO:24). pQE30-Cre contains the Cre recombinase gene, tagged at the N-terminus with the HIV Tat sequence (a protein targeting sequence), cloned into pQE30 (Qiagen) after restriction with BamHI and HindIII. pQE30-Flp contains the Flp recombinase gene, tagged at the N-terminus with the HIV Tat sequence (a protein targeting sequence), cloned into pQE30 (Qiagen) after restriction with BamHI and KpnI.
Figure 4:
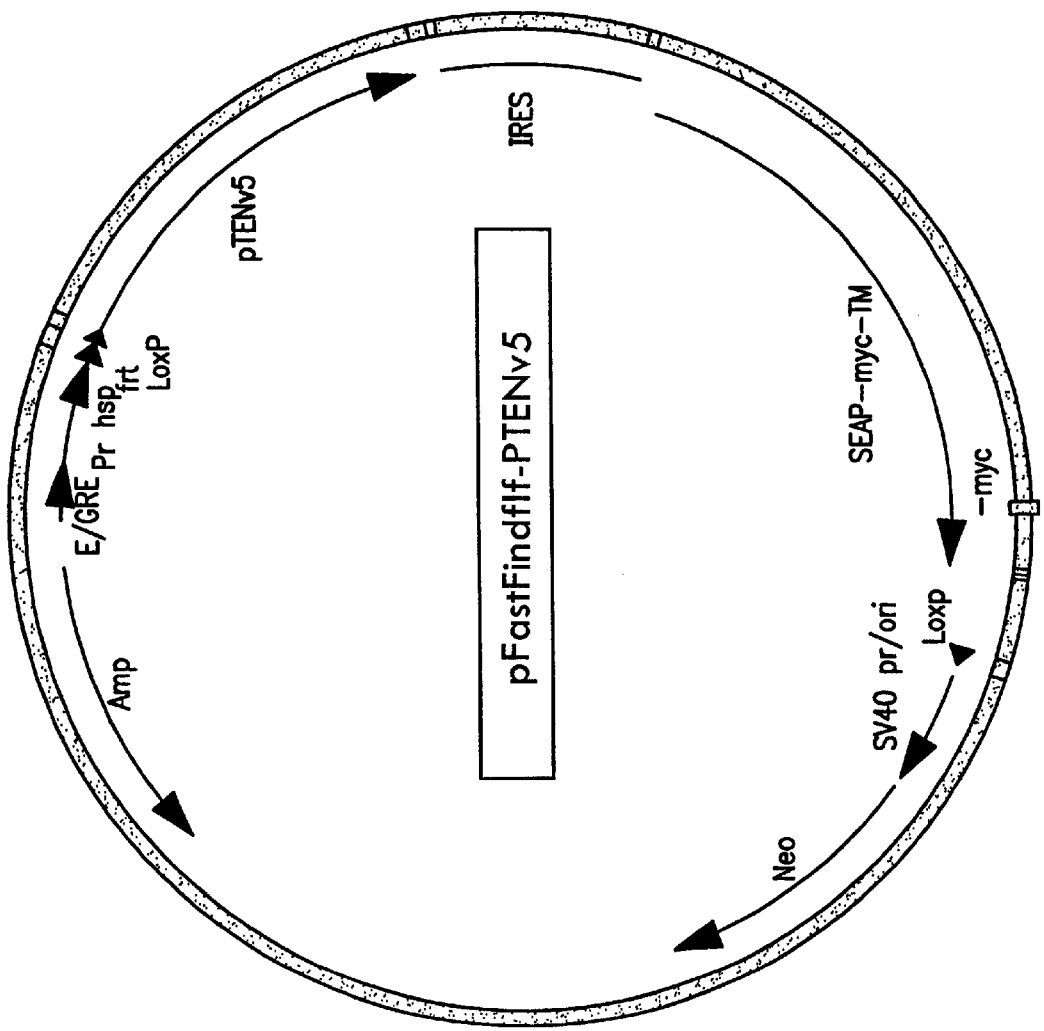
FIG. 4 is a diagram of an embodiment of the invention (pFastFindflf-PTENv5). This vector is the same as pFastFindflf (SEQ ID NO:19) with the addition of the PTEN gene tagged at the C terminus with v5 and placed in the topo cloning site.

The excision process uses the ability of recombinase proteins to delete DNA contained inside direct repeats of the recombinase target sequence. Thus, a cell that contains any of the pFastFindxxx vectors or the FastFindxxSNx (SEQ ID NO:27) can be induced to delete its query gene and cocistronic optically-active marker #1 by transiently transfecting the cell with appropriate recombinase encoding plasmid or providing the recombinase protein by other methods (for example, as a HIV-tat PTD fusion protein). The arrangements of features provided by the pFastFindxxx vectors (FIG. 1) or the pFastFindxxSNx series of vectors allow deletion of the optically-active marker, and in the case of pFastFindxxSNx also the selectable drug marker, along with the query gene. This feature allows the application of powerful cell isolation technologies, including drug selection, FACS and cell panning. These selection strategies allow rapid isolation of the desired query gene-deleted cell line.

The substitution process uses the ability of recombinase proteins to catalyze inter strand DNA recombination using the single recombinase sequence provided by the pFastFindxxx or pFastFindxxSNx series of vectors and a second plasmid provided recombinase target sequence, the pOut-X vectors (FIG. 2). As in the excision case, the recombinase is provided by transiently transfecting the cell with appropriate recombinase encoding plasmid or providing the recombinase protein by other methods, for example as a HIV-tat PTD fusion protein. the arrangements of features provided by the pFastFindxxx vectors or pFastFindxxSNx vectors permit substitution of the optically-active marker #1 and the introduction of a new drug selection marker, along with the query gene. This feature allows the application of powerful cell isolation technologies, including drug selection, FACS and cell panning. These selection strategies allow rapid isolation of the desired query gene-deleted cell line.

EXAMPLES

The following examples are provided as a guide for the practitioner of ordinary skill in the art. Nothing in the examples is intended to limit the claimed invention. Unless otherwise specified, all reagents are used in accordance with the manufacturer's recommendations, and all reactions are performed under standard conditions.

Example 1 pFastFindflf (A) The Plasmid pFastFindflf (SEQ ID NO:19) was Constructed as Follows:

1. Building pFastFind-3'frt. Addition of the 3' frt sequence—the following oligos were used to create an frt sequence downstream of the SEAP-TM of pFastFind:

ALG7=
cgaagttcctattccgaagttcctattctctagaaagtataggaacttcat (SEQ ID NO:3);

ALG8=
taatgaagttcctatactttcta-
gagaataggaacttcggaataggaacttcgcatg (SEQ ID NO:4).

Annealing these two oligos produces a DNA fragment containing the frt sequence, and ends that are compatible with SphI and AseI restriction enzyme sites. This fragment was ligated with the 5.916 kb SphI/RsrII fragment of pFast-Find (which contains the vector backbone, ecdysone inducible promoter, IRES and SEAP/TM sequences) and the 1.056 kb AseI/RsrII fragment of pFastFind (which contains the neomycin resistance gene and SV40 promoter). This construction deletes a 496 bp (basepair) fragment containing the f1 origin of replication located between the SphI and AseI sites downstream of SEAP/TM. The ligated construct was verified by restriction digests.

2. Building pFastFind-5'frt3'frt. The 5'frt sequence was produced by annealing oligos ALG15 and ALG16.

ALG
15=ctagcGAAGTTCCTATTCCGAAGTTCCTATTCT CTAGAAAGTATA-GGAACTTC (SEQ ID NO:5);

ALG
16=ttaaGAAGTTCCTATACTTTCTAGAGAATAGGA ACTTCGGAATAGGA-ACTTCg (SEQ ID NO:6).

Annealing these two oligos produces a DNA fragment that contains the frt sequence and has NheI and AflII compatible restriction sites at its termini. pFastFind3'frt was digested with NheI and AflII and the resulting 7.01 kb fragment was ligated to annealed oligos ALG15 and ALG16 to create pFastFind-5'frt3'frt.

3. Building pFastFindflf. The Loxp sequence was produced by annealing oligos ALG17 and ALG18.

ALG17=TTAAGATAACTTCGTATAATGTATGCTATACG AAGTTATCCCTTA-ATTAATTCCCA (SEQ ID NO:7);

ALG18=CTAGTGGGAATTAATTAAGGGATAACTTCGT ATAGCATACATTAT-ACGAAGTTATC (SEQ ID NO:8).

Annealing these two oligos creates a DNA fragment that contains the Loxp site and has AflII and SpeI compatible restriction sites at its termini. pFastFind-5'frt3'frt was digested with AflII and SpeI and the resulting 7.036 kb fragment was ligated to annealed oligos ALG17 and ALG18 to create pFastFindflf (SEQ ID NO:19).

(B) Building pFastFindflf-PTENv5.

The vector pFastFindflf was digested with PacI and incubated with topoisomerase I (Epicentre). The topoisomerase activated vector was then incubated with a PCR amplified product of PTENv5 which was amplified using the following primers:

HZ82k—ggactagtacaaccatggtgACAGCCATCATCAAAGAG (SEQ ID NO:9);

HZ83—CGCGGTCGACGGCGTCATCATCGTCCTTGTAGTCTC AGACTTTTGTA-ATTTGTG (SEQ ID NO:10). This results in the 8.3 Kb plasmid pFastFindflf-PTENv5.

Example 2 pFastFindxxSNx (A) Building pFastFind with Recyclable Drug Marker.

1. Addition of the 3' frt sequence to pFastFind—the following oligos were used to create an frt sequence downstream of the neomycin gene of pFastFind:

ALG28=cagaagttcctattccgaagttcctattctctagaaagtataggaacttcgg (SEQ ID NO:11);

ALG29=ccgaagttcctatactttctagagaataggaacttcggaataggaacttctg (SEQ ID NO:12).

Annealing these two oligos produces a DNA fragment containing the frt sequence with blunt ends. The base vector, pFastFind, was digested with BstZ17I, a blunt cutter, and ligated to annealed oligos ALG28 and ALG29. Orientation of the frt sequence was determined by PCR amplification, the correct orientation results in the plasmid pFastFind 3"frt.

2. Digest pFastFind 3"frt with BstEII and ScaI to produce a 5.35 kb fragment containing the Neo gene and the 3"frt sequence. Ligate this fragment to the 2.24 kb BstEII—ScaI fragment containing the 5'lox, frt and IRES from pFastFindflf (SEQ ID NO:19x) or pFastFindlff (SEQ ID NO:22). These ligations will create pFastFindflSNf (SEQ ID NO:27) and pFastFindlfSNf respectively.

3. The construction of pFastFind 3"lox, pFastFindflSNl and pFastFindlfSNl was performed in an identical manner as outlined in steps 1 and 2 above with one exception. The oligos ALG30 and ALG31 were annealed and ligated into the BstZ17I site of pFastFind.

ALG30=CAGATAACTTCGTATAATGTATGC-TATACGAAGTTATGG (SEQ ID NO:13);

ALG31=CCATAACTTCGTATAGCATACATTATAC-GAAGTTATCTG (SEQ ID NO:14).

Example 3

Building pOut-flp-cre. pCDNA3.1hygro (Invitrogen) is the base vector for pOut-flp-cre. The CMV promoter was deleted by digesting with BglII and NheI then blunting the ends with Klenow. The vector was then ligated to form pCDNA3.1hygro(-CMV). The 108 bp NheI-SpeI fragment from pFastFindflf was cloned into the SpeI site of pCDNA3.1hygro(-CMV) to create pfl-hygro. The 615 bp XhoI-XhoI fragment from pFastFindflf containing the IRES was then blunted with Klenow and cloned into the 4.83 Kb EcoRV digested pfl-hygro vector to produce pfl-IRES-hygro. Surface marker #2 was then PCR amplified with SrfI-NotI ends and ligated into pfl-IRES-Hygro to create pOut-flp-cre.

Example 4

Building Recombinase Producing Vectors (A) Building pQE30Flip.

The FLIP gene was PCR amplified using the following primers:

DAS5flptg=GGAAGATCTTATGGTCGCAAAAAACGCCGTCA-GCGCCGTCGTGGCCCA-CAATTTGATATATTATGTAAAACAC (SEQ ID NO:15);

DAS3flp=CGGGGTACCTTATATGCGTCTATTTATGTA (SEQ ID NO:16).

The PCR product was then cloned into pCDNA3.1. The Flip gene was isolated from pcDNA3.1Flip2 by digesting with BglII and KpnI. The resulting 1.31 kb fragment was directionally cloned into pQE30 (Qiagen) digested with BamHI and KpnI producing pQE30Flip.

(B) Building pQE30Cre.

The Cre gene was PCR amplified from pBS 185 (Life Technologies) using the following primers:

DAS5cretg=GGAAGATCTTATGGTCGCAAAAAACGC-CGTCAGCGC CGTCGTGGCTCCAATTTACTGAC-CGTACACCAAAATTTGCCT (SEQ ID NO:17);

DAS3cre=CCCAAGCTTCTAATCGCCATCTTCCAG-CAGGCGCACCAT (SEQ ID NO:20).

The PCR product was then cloned into pcDNA3.1. The Cre gene was isolated from pcDNA3.1Cre2 by digesting with BglII and HindIII. The resulting 1.07 kb fragment was directionally cloned into pQE30 (Qiagen) digested with BamHI and HindIII producing pQE30Cre.

Example 5 pCMVstopLacZ (A) Building pCMVstopLacZ.

The pDisplay vector was digested with EcoRI and XhoI to produce a 5 Kb fragment. This fragment was ligated with a 1.47 Kb EcoRI-SpeI fragment from pBS302 containing a translational stop cassette flanked by Loxp sites and a 3.13 Kb SpeI-XhoI fragment from pCMVLacZ containing the beta galactosidase gene from E. coli. This ligation results in a 9.58 Kb vector pCMVstopLacZ.

Example 6

Delivery of Query Gene

The query gene is cloned into the chosen pFastFind vector of choice by methods including, but not limited to, topocloning, TA cloning and standard cloning utilizing restriction enzymes. Once the delivery vector contains the query gene of interest, it is delivered to the mammalian cells by methods including, but not limited to, electroporation, lipofectant mediated transfection, calcium phosphate mediated transfection, retroviral infection, and adenoviral infection. Following introduction of the query gene, addition of neomycin to the culture medium selects against cells that failed to incorporate the query gene-containing vector. Cells successfully incorporating the vector, which contains the neomycin-resistance drug marker (or other drug resistance marker), continue to proliferate in the medium supplemented with G418. Finally, cells with inducible expression of the query gene are sorted from the selected population. This is accomplished by addition of inducer (ponasterone), and staining for the transcriptionally linked optically-active marker using appropriate antibodies. The cells staining with the anti-marker #1 antibody are sorted from the unstained cells by Fluorescence activated cell sorting (FACS).

Example 7

Protein Delivery System

The Cre and Flip recombinase proteins are produced from the vectors pQE30Cre and pQE30Flip, respectively, and purified utilizing the 6-Histidine tag at their N-terminus. Concentrated proteins are applied to the cells, either in unison with the appropriate pOut vector to insert an alternate DNA sequence, or alone to delete the query gene by methods including, but not limited to, electroporation, lipofectant-mediated transfection, and calcium phosphate-mediated transfection. The activity of the Cre protein can be monitored in vivo with the pCMVstopLacZ test vector. A functioning Cre protein acts on the loxp sites flanking the stop cassette and deletes this sequence from the vector. The result of the stop cassette deletion is a constitutively active beta-galactosidase gene which can be monitored by FACS or chemical staining.

Example 8

Deletion of Query Gene

The pFastFindxxx vectors have loxp or frt sequences flanking the query gene and transcriptionally-linked optically-active marker. The addition of Cre or Flp recombinase catalyzes the excision event of the DNA sequences located between the loxp or frt sequences, respectively. To enrich for cells successfully deleting the query gene, the population of cells that fail to stain for the optically-active marker is sorted and cloned or pooled using FACS. The loss of both the query gene and optically-active marker can be verified by methods including but not limited to PCR or Southern analysis.

Example 9

Replacement of Query Gene

The pFastFind vectors have both a loxp and frt sequence located between the query gene cloning site and the promoter elements. The Cre and Flp recombinases are capable of catalyzing recombination between two unlinked DNA molecules if each molecule contains the loxp or frt target sequences, respectively. The Cre-Out vector is a promoter-less vector containing a loxp site upstream of the cloning site. An altered form of the query gene can be cloned into the Cre-Out vector between the loxp site and the transcriptionally linked optically-active marker (e.g. HA) by methods including but not limited to topocloning, TA-cloning, or standard cloning. Once the Cre-Out vector contains the altered gene of interest it is delivered to the mammalian cells together with the Cre protein or Cre protein-producing plasmid by methods including but not limited to electroporation, lipofectant mediated transfection, calcium phosphate mediated transfection, retroviral infection, and adenoviral infection.

Following introduction of the altered query gene, addition of hygromycin to the culture medium selects against cells that failed to incorporate the Out-vector. Cells successfully incorporating the vector, which contains the Hygromycin-resistance drug marker (or other drug resistance marker), will continue to proliferate in the medium supplemented with hygromycin. Finally, cells with inducible expression of the altered query gene are sorted from the selected population. This is accomplished by adding inducer (ponasterone), and staining for the transcriptionally linked surface marker #2 using appropriate antibodies. The cells that stain with the anti-surface marker #2 antibody and fail to stain with anti-surface marker #1 are sorted from the cell population by FACS. The replacement of the query gene can be verified by methods including but not limited to PCR or Southern analysis.

Example 10

Recycling the drug marker

The neomycin resistance drug marker located on the pFastFindxxSNx—type vectors may be recycled while removing the query gene and surface marker #1. This is accomplished as described above in (I) for the removal of the query gene. The pFastFindxxSNx vectors have loxp or frt sequences flanking the query gene, transcriptionally-linked surface marker and the neomycin resistance gene. The addition of Cre or Flip recombinase catalyzes the excision event of the DNA sequences located between the loxp or frt sequences, respectively. To enrich for cells successfully deleting the query gene, the population of cells that fail to stain for surface marker #1 can be sorted and cloned or pooled using FACS. The loss of both the query gene and surface marker can be verified by methods including but not limited to PCR or Southern analysis.

What is claimed:

1. A polynucleotide vector, comprising in order of transcription:
   a) a regulatable promoter;
   b) a first recombinase target sequence;
   c) a second recombinase target sequence different from said first recombinase target sequence;
   d) a cloning site suitable for insertion of a test gene;
   e) an internal ribosome binding site (IRES);
   f) a optically-active marker-encoding sequence; and g) a third recombinase target sequence homologous to either said first recombinase target sequence or said second recombinase target sequence.

2. The vector of claim 1, further comprising a second promoter, and a selectable marker operatively associated with said second promoter.

3. The vector of claim 2, wherein said second promoter and selectable marker are positioned downstream from said third recombinase target sequence.

4. The vector of claim 2, wherein said second promoter and selectable marker are positioned between said optically-active marker sequence and said third recombinase target sequence.

5. The vector of claim 1, further comprising a test gene inserted at said cloning site.

6. A method of selecting a host cell having a functioning test gene, comprising:

a) providing a host cell lacking a functioning test gene;
b) inserting into said host cell a vector, said vector comprising a regulatable promoter; a first recombinase target sequence; a second recombinase target sequence different from said first recombinase target sequence; a test gene; an internal ribosome binding site (IRES); a label sequence encoding a detectable marker; and a third recombinase target sequence homologous to either said first recombinase target sequence or said second recombinase target sequence;
c) selecting against cells that failed to incorporate said vector;
d) inducing said regulatable promoter; and
e) selecting for cells that express said detectable marker.

7. The method of claim 6, further comprising:
f) contacting said host cell with a recombinase capable of catalyzing excision of said label sequence.

* * * * *

SEQUENCE LISTING

<160> NUMBER OF SEQ ID NOS: 27

<210> SEQ ID NO 1
<211> LENGTH: 34
<212> TYPE: DNA
<213> ORGANISM: enzyme recognition site

<400> SEQUENCE: 1
ataacttcgt ataatgtatg ctatacgaag ttat                              34

<210> SEQ ID NO 2
<211> LENGTH: 11
<212> TYPE: PRT
<213> ORGANISM: Human immunodeficiency virus

<400> SEQUENCE: 2

Tyr Gly Arg Lys Lys Arg Arg Gln Arg Arg Arg
1               5                   10

<210> SEQ ID NO 3
<211> LENGTH: 51
<212> TYPE: DNA
<213> ORGANISM: PCR primer

<400> SEQUENCE: 3
cgaagttcct attccgaagt tcctattctc tagaaagtat aggaacttca t           51

<210> SEQ ID NO 4
<211> LENGTH: 51
<212> TYPE: DNA
<213> ORGANISM: PCR primer

<400> SEQUENCE: 4
cgaagttcct attccgaagt tcctattctc tagaaagtat aggaacttca t           51

<210> SEQ ID NO 5
<211> LENGTH: 53
<212> TYPE: DNA
<213> ORGANISM: PCR primer

<400> SEQUENCE: 5
ctagcgaagt tcctattccg aagttcctat tctctagaaa gtataggaac ttc         53

<210> SEQ ID NO 6
<211> LENGTH: 53
<212> TYPE: DNA
<213> ORGANISM: PCR primer

<400> SEQUENCE: 6
ttaagaagtt cctatacttt ctagagaata ggaacttcgg aataggaact tcg         53

<210> SEQ ID NO 7
<211> LENGTH: 56
<212> TYPE: DNA
<213> ORGANISM: PCR primer

<400> SEQUENCE: 7
ttaagataac ttcgtataat gtatgctata cgaagttatc ccttaattaa ttccca      56

<210> SEQ ID NO 8
<211> LENGTH: 56
<212> TYPE: DNA

<213> ORGANISM: PCR primer

<400> SEQUENCE: 8
ctagtgggaa ttaattaagg gataacttcg tatagcatac attatacgaa gttatc        56

<210> SEQ ID NO 9
<211> LENGTH: 38
<212> TYPE: DNA
<213> ORGANISM: PCR primer

<400> SEQUENCE: 9
ggactagtac aaccatggtg acagccatca tcaaagag        38

<210> SEQ ID NO 10
<211> LENGTH: 54
<212> TYPE: DNA
<213> ORGANISM: PCR primer

<400> SEQUENCE: 10
cgcggtcgac ggcgtcatca tcgtccttgt agtctcagac ttttgtaatt tgtg        54

<210> SEQ ID NO 11
<211> LENGTH: 52
<212> TYPE: DNA
<213> ORGANISM: PCR primer

<400> SEQUENCE: 11
cagaagttcc tattccgaag ttcctattct ctagaaagta taggaacttc gg        52

<210> SEQ ID NO 12
<211> LENGTH: 52
<212> TYPE: DNA
<213> ORGANISM: PCR primer

<400> SEQUENCE: 12
ccgaagttcc tatactttct agagaatagg aacttcggaa taggaacttc tg        52

<210> SEQ ID NO 13
<211> LENGTH: 39
<212> TYPE: DNA
<213> ORGANISM: PCR primer

<400> SEQUENCE: 13
cagataactt cgtataatgt atgctatacg aagttatgg        39

<210> SEQ ID NO 14
<211> LENGTH: 39
<212> TYPE: DNA
<213> ORGANISM: PCR primer

<400> SEQUENCE: 14
ccataacttc gtatagcata cattatacga agttatctg        39

<210> SEQ ID NO 15
<211> LENGTH: 73
<212> TYPE: DNA
<213> ORGANISM: PCR primer

<400> SEQUENCE: 15
ggaagatctt atggtcgcaa aaaacgccgt cagcgccgtc gtggcccaca atttgatata        60
ttatgtaaaa cac        73

```
<210> SEQ ID NO 16
<211> LENGTH: 30
<212> TYPE: DNA
<213> ORGANISM: PCR primer

<400> SEQUENCE: 16
cggggtacct tatatgcgtc tatttatgta                                          30

<210> SEQ ID NO 17
<211> LENGTH: 78
<212> TYPE: DNA
<213> ORGANISM: PCR primer

<400> SEQUENCE: 17
ggaagatctt atggtcgcaa aaacgccgt cagcgccgtc gtggctccaa tttactgacc          60
gtacaccaaa atttgcct                                                       78

<210> SEQ ID NO 18
<211> LENGTH: 39
<212> TYPE: DNA
<213> ORGANISM: PCR primer

<400> SEQUENCE: 18
cccaagcttc taatcgccat cttccagcag gcgcaccat                                39

<210> SEQ ID NO 19
<211> LENGTH: 7092
<212> TYPE: DNA
<213> ORGANISM: vector

<400> SEQUENCE: 19
agatctcggc cgcatattaa gtgcattgtt ctcgataccg ctaagtgcat tgttctcgtt         60
agctcgatgg acaagtgcat tgttctcttg ctgaaagctc gatggacaag tgcattgttc        120
tcttgctgaa agctcgatgg acaagtgcat tgttctcttg ctgaaagctc agtacccggg        180
agtaccctcg accgccggag tataaataga ggcgcttcgt ctacggagcg acaattcaat        240
tcaaacaagc aaagtgaaca cgtcgctaag cgaaagctaa gcaaataaac aagcgcagct        300
gaacaagcta acaatctgc  agtaaagtgc aagttaaagt gaatcaatta aaagtaacca        360
gcaaccaagt aaatcaactg caactactga aatctgccaa gaagtaatta ttgaatacaa        420
gaagagaact ctgaatactt tcaacaagtt accgagaaag aagaactcac acacagctag        480
cgaagttcct attccgaagt tcctattctc tagaaagtat aggaacttct aagataact         540
tcgtataatg tatgctatac gaagttatcc cttaattaat tcccactagt ccagtgtggt        600
ggaattctgc agatatccag cacagtggcg gccgctcgag ccaattccgc ccctctcccc        660
cccccccccc taacgttact ggccgaagcc gcttggaata aggccggtgt gcgtttgtct        720
atatgtgatt ttccaccata ttgccgtctt ttggcaatgt gagggcccgg aaacctggcc        780
ctgtcttctt gacgagcatt cctaggggtc tttcccctct cgccaaagga atgcaaggtc        840
tgttgaatgt cgtgaaggaa gcagttcctc tggaagcttc ttgaagacaa acaacgtctg        900
tagcgaccct ttgcaggcag cggaaccccc cacctggcga caggtgcctc tgcggccaaa        960
agccacgtgt ataagataca cctgcaaagg cggcacaacc ccagtgccac gttgtgagtt       1020
ggatagttgt ggaaagagtc aaatggctct cctcaagcgt attcaacaag ggctgaagg        1080
atgcccagaa ggtaccccat tgtatgggat ctgatctggg gcctcggtgc acatgcttta       1140
catgtgttta gtcgaggtta aaaaaacgtc taggcccccc gaaccacggg gacgtggttt       1200
```

-continued

```
tcctttgaaa aacacgatga taagcttgcc acaacccggt ctagcccggg ctcgagatct    1260
gcgatctaag taagcttcga atcgcgaatt cgcccaccat gctgctgctg ctgctgctgc    1320
tgggcctgag gctacagctc tccctgggca tcatcccagt tgaggaggag aacccggact    1380
tctggaaccg cgaggcagcc gaggccctgg gtgccgccaa gaagctgcag cctgcacaga    1440
cagccgccaa gaacctcatc atcttcctgg gcgatgggat ggggtgtct acggtgacag    1500 ctgccaggat cctaaaaggg cagaagaagg acaaactggg gcctgagata ccctggcca    1560 tggaccgctt cccatatgtg gctctgtcca agacatacaa tgtagacaaa catgtgccag    1620
acagtggagc cacagccacg gcctacctgt gcgggtcaa gggcaacttc cagaccattg    1680
gcttgagtgc agccgcccgc tttaaccagt gcaacgac acgcggcaac gaggtcatct    1740
ccgtgatgaa tcgggccaag aaagcaggga agtcagtggg agtggtaacc accacacgag    1800
tgcagcacgc ctcgccagcc ggcacctacg cccacgggt gaaccgcaac tggtactcgg    1860
acgccgacgt gcctgcctcg gcccgccagg aggggtgcca ggacatcgct acgcagctca    1920
tctccaacat ggacattgac gtgatcctag gtggaggccg aaagtacatg tttcgcatgg    1980 gaacccaga ccctgagtac ccagatgact acagccaagg tgggaccagg ctggacggga    2040
agaatctggt gcaggaatgg ctggcgaagc gccagggtgc ccgtatgtg tggaaccgca    2100 ctgagctcat gcaggcttcc ctggacccgt ctgtgaccca tctcatgggt ctctttgagc    2160
ctggagacat gaaatacgag atccaccgag actccacact ggaccctcc ctgatggaga    2220 tgacagaggc tgccctgcgc ctgctgagca ggaaccccg cggcttcttc ctcttcgtgg    2280
agggtggtcg catcgaccat ggtcatcatg aaagcaggc ttaccgggca ctgactgaga    2340
cgatcatgtt cgacgacgcc attgagaggg cgggccagct caccagcgag gaggacacgc    2400
tgagcctcgt cactgccgac cactcccacg tcttctcctt cggaggctac cccctgcgag    2460
ggagctccat cttcgggctg gcccctggca aggcccggga caggaaggcc tacacggtcc    2520
tcctatacgg aaacggtcca ggctatgtgc tcaaggacgg cgcccggccg gatgttaccg    2580
agagcgagag cgggagcccc gagtatcggc agcagtcagc agtgccctg gacgaagaga    2640 cccacgcagg cgaggacgtg gcggtgttcg cgcgcggccc gcaggcgcac ctggttcacg    2700
gcgtgcagga gcagaccttc atagcgcacg tcatggcctt cgccgcctgc ctggagccct    2760
acaccgcctg cgacctggcg cccccgccg gcaccaccga cgccgcgcac ccgggttact    2820
ctagagtcgg ggcggccggc cgcttcgagc agacatctcc cgggaatccg cggctgcagg    2880
tcgacgaaca aaaactcatc tcagaagagg atctgaatgc tgtgggccag gacacgcagg    2940
aggtcatcgt ggtgccacac tccttgccct ttaaggtggt ggtgatctca gccatcctgg    3000
ccctggtggt gctcaccatc atctccctta tcatcctcat catgctttgg cagaagaagc    3060
cacgttaggc ggccgctcga gatcagctag agggcccgtt taaacccgct gatcagcctc    3120
gactgtgcct tctagttgcc agccatctgt tgtttgcccc tcccccgtgc cttccttgac    3180
cctggaaggt gccactccca ctgtccttc ctaataaaat gaggaaattg catcgcattg    3240
tctgagtagg tgtcattcta ttctgggggg tggtgggg caggacagca aggggagga    3300 ttgggaagac aatagcaggc atgcgaagtt cctattccga agttcctatt ctctagaaag    3360
tataggaact tcattaattc tgtggaatgt gtgtcagtta gggtgtggaa agtccccagg    3420 ctcccccaggc aggcagaagt atgcaaagca tgcatctcaa ttagtcagca accaggtgtg    3480
gaaagtcccc aggctcccca gcaggcagaa gtatgcaaag catgcatctc aattagtcag    3540
caaccatagt cccgcccta actccgccca tcccgccct aactccgccc agttccgccc    3600
```

-continued

```
attctccgcc ccatggctga ctaattttttt ttatttatgc agaggccgag gccgcctctg    3660
cctctgagct attccagaag tagtgaggag gctttttttgg aggcctaggc ttttgcaaaa    3720
agctcccggg agcttgtata tccatttttcg gatctgatca agagacagga tgaggatcgt    3780
ttcgcatgat tgaacaagat ggattgcacg caggttctcc ggccgcttgg gtggagaggc    3840
tattcggcta tgactgggca caacagacaa tcggctgctc tgatgccgcc gtgttccggc    3900
tgtcagcgca ggggcgcccg gttctttttg tcaagaccga cctgtccggt gccctgaatg    3960
aactgcagga cgaggcagcg cggctatcgt ggctggccac gacgggcgtt ccttgcgcag    4020
ctgtgctcga cgttgtcact gaagcgggaa gggactggct gctattgggc gaagtgccgg    4080
ggcaggatct cctgtcatct caccttgctc ctgccgagaa agtatccatc atggctgatg    4140
caatgcggcg gctgcatacg cttgatccgg ctacctgccc attcgaccac caagcgaaac    4200
atcgcatcga gcgagcacgt actcggatgg aagccggtct tgtcgatcag gatgatctgg    4260
acgaagagca tcaggggctc gcgccagccg aactgttcgc caggctcaag gcgcgcatgc    4320
ccgacggcga ggatctcgtc gtgacccatg gcgatgcctg cttgccgaat atcatggtgg    4380
aaaatggccg cttttctgga ttcatcgact gtggccggct gggtgtggcg gaccgctatc    4440
aggacatagc gttggctacc cgtgatattg ctgaagagct tggcggcgaa tgggctgacc    4500
gcttcctcgt gctttacggt atcgccgctc ccgattcgca gcgcatcgcc ttctatcgcc    4560
ttcttgacga gttcttctga gcgggactct ggggttcgaa atgaccgacc aagcgacgcc    4620
caacctgcca tcacgagatt tcgattccac cgccgccttc tatgaaaggt tgggcttcgg    4680
aatcgttttc cgggacgccg gctggatgat cctccagcgc ggggatctca tgctggagtt    4740
cttcgcccac cccaacttgt ttattgcagc ttataatggt tacaaataaa gcaatagcat    4800
cacaaatttc acaaataaag catttttttc actgcattct agttgtggtt tgtccaaact    4860
catcaatgta tcttatcatg tctgtatacc gtcgacctct agctagagct tggcgtaatc    4920
atggtcatag ctgtttcctg tgtgaaattg ttatccgctc acaattccac acaacatacg    4980
agccggaagc ataaagtgta aagcctgggg tgcctaatga gtgagctaac tcacattaat    5040
tgcgttgcgc tcactgcccg ctttccagtc gggaaacctg tcgtgccagc tgcattaatg    5100
aatcggccaa cgcgcgggga gaggcggttt gcgtattggg cgctcttccg cttcctcgct    5160
cactgactcg ctgcgctcgg tcgttcggct gcggcgagcg gtatcagctc actcaaaggc    5220
ggtaatacgg ttatccacag aatcagggga taacgcagga aagaacatgt gagcaaaagg    5280
ccagcaaaag gccaggaacc gtaaaaaggc cgcgttgctg gcgttttttcc ataggctccg    5340 cccccctgac gagcatcaca aaaatcgacg ctcaagtcag aggtggcgaa acccgacagg    5400
actataaaga taccaggcgt ttccccctgg aagctccctc gtgcgctctc ctgttccgac    5460
cctgccgctt accggatacc tgtccgcctt tctcccttcg ggaagcgtgg cgctttctca    5520
atgctcacgc tgtaggtatc tcagttcggt gtaggtcgtt cgctccaagc tgggctgtgt    5580
gcacgaaccc cccgttcagc ccgaccgctg cgccttatcc ggtaactatc gtcttgagtc    5640
caacccggta agacacgact tatcgccact ggcagcagcc actggtaaca ggattagcag    5700
agcgaggtat gtaggcggtg ctacagagtt cttgaagtgg tggcctaact acggctacac    5760
tagaaggaca gtatttggta tctgcgctct gctgaagcca gttaccttcg gaaaaagagt    5820
tggtagctct tgatccggca aacaaaccac cgctggtagc ggtggttttt ttgtttgcaa    5880
gcagcagatt acgcgcagaa aaaaggatc tcaagaagat cctttgatct tttctacggg    5940
```

```
gtctgacgct cagtggaacg aaaactcacg ttaagggatt ttggtcatga gattatcaaa   6000
aaggatcttc acctagatcc ttttaaatta aaaatgaagt tttaaatcaa tctaaagtat   6060
atatgagtaa acttggtctg acagttacca atgcttaatc agtgaggcac ctatctcagc   6120
gatctgtcta tttcgttcat ccatagttgc ctgactcccc gtcgtgtaga taactacgat   6180
acgggagggc ttaccatctg gccccagtgc tgcaatgata ccgcgagacc cacgctcacc   6240
ggctccagat ttatcagcaa taaaccagcc agccggaagg gccgagcgca gaagtggtcc   6300
tgcaacttta tccgcctcca tccagtctat taattgttgc cgggaagcta gagtaagtag   6360
ttcgccagtt aatagtttgc gcaacgttgt tgccattgct acaggcatcg tggtgtcacg   6420
ctcgtcgttt ggtatggctt cattcagctc cggttcccaa cgatcaaggc gagttacatg   6480
atcccccatg ttgtgcaaaa aagcggttag ctccttcggt cctccgatcg ttgtcagaag   6540
taagttggcc gcagtgttat cactcatggt tatggcagca ctgcataatt ctcttactgt   6600
catgccatcc gtaagatgct tttctgtgac tggtgagtac tcaaccaagt cattctgaga   6660
atagtgtatg cggcgaccga gttgctcttg cccggcgtca atacgggata ataccgcgcc   6720
acatagcaga actttaaaag tgctcatcat tggaaaacgt tcttcggggc gaaaactctc   6780
aaggatctta ccgctgttga tccagttcga tgtaaccc actcgtgcac ccaactgatc   6840
ttcagcatct tttactttca ccagcgtttc tgggtgagca aaaacaggaa ggcaaaatgc   6900
cgcaaaaaag ggaataaggg cgacacggaa atgttgaata ctcatactct tcctttttca   6960
atattattga agcatttatc agggttattg tctcatgagc ggatacatat ttgaatgtat   7020
ttagaaaaat aaacaaatag gggttccgcg cacatttccc cgaaaagtgc cacctgacgt   7080
cgacggatcg gg                                                       7092

<210> SEQ ID NO 20
<211> LENGTH: 7076
<212> TYPE: DNA
<213> ORGANISM: vector

<400> SEQUENCE: 20
agatctcggc cgcatattaa gtgcattgtt ctcgataccg ctaagtgcat tgttctcgtt     60
agctcgatgg acaagtgcat tgttctcttg ctgaaagctc gatggacaag tgcattgttc    120
tcttgctgaa agctcgatgg acaagtgcat tgttctcttg ctgaaagctc agtacccggg    180
agtaccctcg accgccggag tataaataga ggcgcttcgt ctacgagcg acaattcaat    240 tcaaacaagc aaagtgaaca cgtcgctaag cgaaagctaa gcaaataaac aagcgcagct    300
gaacaagcta acaatctgc agtaaagtgc aagttaaagt gaatcaatta aaagtaacca    360
gcaaccaagt aaatcaactg caactactga atctgccaa gaagtaatta ttgaatacaa    420
gaagagaact ctgaatactt tcaacaagtt accgagaaag aagaactcac acacagctag    480
cgaagttcct attccgaagt tcctattctc tagaaagtat aggaacttct aagataact    540 tcgtataatg tatgctatac gaagttatcc cttaattaat tcccactagt ccagtgtggt    600
ggaattctgc agatatccag cacagtggcg gccgctcgag ccaattccgc cctctcccct    660 ccccccccc taacgttact ggccgaagcc gcttggaata aggccggtgt gcgtttgtct    720
atatgtgatt ttccaccata ttgccgtctt ttggcaatgt gagggcccgg aaacctggcc    780
ctgtcttctt gacgagcatt cctagggtc ttttcccctct cgccaaagga atgcaaggtc    840
tgttgaatgt cgtgaaggaa gcagttcctc tggaagcttt tgaagacaa acaacgtctg    900 tagcgaccct ttgcaggcag cggaaccccc cacctggcga caggtgcctc tgcggccaaa    960
```

```
agccacgtgt ataagataca cctgcaaagg cggcacaacc ccagtgccac gttgtgagtt    1020
ggatagttgt ggaaagagtc aaatggctct cctcaagcgt attcaacaag gggctgaagg    1080
atgcccagaa ggtaccccat tgtatgggat ctgatctggg gcctcggtgc acatgcttta    1140
catgtgttta gtcgaggtta aaaaaacgtc taggccccc gaaccacggg gacgtggttt    1200
tcctttgaaa aacacgatga taagcttgcc acaacccggt ctagcccggg ctcgagatct    1260
gcgatctaag taagcttcga atcgcgaatt cgcccaccat gctgctgctg ctgctgctgc    1320
tgggcctgag gctacagctc tccctgggca tcatcccagt tgaggaggag aacccggact    1380
tctggaaccg cgaggcagcc gaggccctgg gtgccgccaa gaagctgcag cctgcacaga    1440
cagccgccaa gaacctcatc atcttcctgg gcgatgggat gggggtgtct acggtgacag    1500
ctgccaggat cctaaaaggg cagaagaagg acaaactggg gcctgagata cccctggcca    1560
tggaccgctt cccatatgtg gctctgtcca agacatacaa tgtagacaaa catgtgccag    1620
acagtggagc cacagccacg gcctacctgt gcggggtcaa gggcaacttc cagaccattg    1680
gcttgagtgc agccgcccgc tttaaccagt gcaacacgac acgcggcaac gaggtcatct    1740
ccgtgatgaa tcgggccaag aaagcaggga gtcagtgggg agtggtaacc accacacgag    1800
tgcagcacgc ctcgccagcc ggcacctacg cccacacggt gaaccgcaac tggtactcgg    1860
acgccgacgt gcctgcctcg gcccgccagg aggggtgcca ggacatcgct acgcagctca    1920
tctccaacat ggacattgac gtgatcctag gtggaggccg aaagtacatg tttcgcatgg    1980
gaaccccaga ccctgagtac ccagatgact acagccaagg tgggaccagg ctggacggga    2040
agaatctggt gcaggaatgg ctggcgaagc gccagggtgc ccgtatgtgt ggaaccgca    2100
ctgagctcat gcaggcttcc ctggacccgt ctgtgaccca tctcatgggt ctctttgagc    2160
ctggagacat gaaatacgag atccaccgag actccacact ggaccctcc ctgatggaga    2220
tgacagaggc tgccctgcgc ctgctgagca ggaacccccg cggcttcttc ctcttcgtgg    2280
agggtggtcg catcgaccat ggtcatcatg aaagcagggc ttaccgggca ctgactgaga    2340
cgatcatgtt cgacgacgcc attgagaggg cgggccagct caccagcgag gaggacacgc    2400
tgagcctcgt cactgccgac cactcccacg tcttctcctt cggaggctac ccctgcgag    2460
ggagctccat cttcgggctg gcccctggca aggcccggga caggaaggcc tacacggtcc    2520
tcctatacgg aaacggtcca ggctatgtgc tcaaggacgg cgcccggccg gatgttaccg    2580
agagcgagag cggagccccc gagtatcggc agcagtcagc agtgcccctg acgaagaga    2640
cccacgcagg cgaggacgtg gcggtgttcg cgcgcggccc gcaggcgcac ctggttcacg    2700
gcgtgcagga gcagaccttc atagcgcacg tcatggcctt cgccgcctgc ctggagccct    2760
acaccgcctg cgacctggcg ccccccgccg gcaccaccga cgccgcgcac ccgggttact    2820
ctagagtcgg ggcggccggc cgcttcgagc agacatctcc cgggaatccg cggctgcagg    2880
tcgacgaaca aaaactcatc tcagaagagg atctgaatgc tgtgggccag gacacgcagg    2940
aggtcatcgt ggtgccacac tccttgccct ttaaggtggt ggtgatctca gccatcctgg    3000
ccctggtggt gctcaccatc atctccctta tcatcctcat catgctttgg cagaagaagc    3060
cacgttaggc ggccgctcga gatcagctag agggcccgtt taaacccgct gatcagcctc    3120
gactgtgcct tctagttgcc agccatctgt tgtttgcccc tcccccgtgc cttccttgac    3180
cctggaaggt gccactccca ctgtcctttc ctaataaaat gaggaaattg catcgcattg    3240
tctgagtagg tgtcattcta ttctgggggg tggggtgggg caggacagca agggggagga    3300
```

-continued

```
ttgggaagac aatagcaggc atgcataact tcgtataatg tatgctatac gaagttatta      3360
attctgtgga atgtgtgtca gttagggtgt ggaaagtccc caggctcccc aggcaggcag      3420
aagtatgcaa agcatgcatc tcaattagtc agcaaccagg tgtggaaagt ccccaggctc      3480
cccagcaggc agaagtatgc aaagcatgca tctcaattag tcagcaacca tagtcccgcc      3540
cctaactccg cccatcccgc ccctaactcc gcccagttcc gcccattctc cgccccatgg      3600
ctgactaatt tttttatttt atgcagaggc cgaggccgcc tctgcctctg agctattcca      3660
gaagtagtga ggaggctttt ttggaggcct aggcttttgc aaaaagctcc cgggagcttg      3720
tatatccatt ttcggatctg atcaagagac aggatgagga tcgtttcgca tgattgaaca      3780
agatggattg cacgcaggtt ctccggccgc ttgggtggag aggctattcg gctatgactg      3840
ggcacaacag acaatcggct gctctgatgc cgccgtgttc cggctgtcag cgcaggggcg      3900
cccggttctt tttgtcaaga ccgacctgtc cggtgccctg aatgaactgc aggacgaggc      3960
agcgcggcta tcgtggctgg ccacgacggg cgttccttgc gcagctgtgc tcgacgttgt      4020
cactgaagcg ggaagggact ggctgctatt gggcgaagtg ccggggcagg atctcctgtc      4080
atctcacctt gctcctgccg agaaagtatc catcatggct gatgcaatgc ggcggctgca      4140
tacgcttgat ccggctacct gcccattcga ccaccaagcg aaacatcgca tcgagcgagc      4200
acgtactcgg atgaagccgg tcttgtcga tcaggatgat ctggacgaag agcatcaggg      4260
gctcgcgcca gccgaactgt tcgccaggct caaggcgcgc atgcccgacg gcgaggatct      4320
cgtcgtgacc catggcgatg cctgcttgcc gaatatcatg gtggaaaatg gccgcttttc      4380
tggattcatc gactgtggcc ggctgggtgt ggcggaccgc tatcaggaca tagcgttggc      4440
tacccgtgat attgctgaag agcttggcgg cgaatgggct gaccgcttcc tcgtgcttta      4500
cggtatcgcc gctcccgatt cgcagcgcat cgccttctat cgccttcttg acgagttctt      4560
ctgagcggga ctctggggtt cgaaatgacc gaccaagcga cgcccaacct gccatcacga      4620
gatttcgatt ccaccgccgc cttctatgaa aggttgggct tcggaatcgt tttccgggac      4680
gccggctgga tgatcctcca gcgcggggat ctcatgctgg agttcttcgc ccaccccaac      4740
ttgtttattg cagcttataa tggttacaaa taaagcaata gcatcacaaa tttcacaaat      4800
aaagcatttt tttcactgca ttctagttgt ggtttgtcca aactcatcaa tgtatcttat      4860
catgtctgta taccgtcgac ctctagctag agcttggcgt aatcatggtc atagctgttt      4920
cctgtgtgaa attgttatcc gctcacaatt ccacacaaca tacgagccgg aagcataaag      4980
tgtaaagcct ggggtgccta atgagtgagc taactcacat taattgcgtt gcgctcactg      5040
cccgctttcc agtcgggaaa cctgtcgtgc cagctgcatt aatgaatcgg ccaacgcgcg      5100
gggagaggcg gtttgcgtat tgggcgctct tccgcttcct cgctcactga ctcgctgcgc      5160
tcggtcgttc ggctgcggcg agcggtatca gctcactcaa aggcggtaat acggttatcc      5220
acagaatcag gggataacgc aggaaagaac atgtgagcaa aaggccagca aaaggccagg      5280
aaccgtaaaa aggccgcgtt gctggcgttt ttccataggc tccgcccccc tgacgagcat      5340
cacaaaaatc gacgctcaag tcagaggtgg cgaaacccga caggactata aagataccag      5400
gcgtttcccc ctggaagctc cctcgtgcgc tctcctgttc cgaccctgcc gcttaccgga      5460
tacctgtccg cctttctccc ttcgggaagc gtggcgcttt ctcaatgctc acgctgtagg      5520
tatctcagtt cggtgtaggt cgttcgctcc aagctgggct gtgtgcacga accccccgtt      5580
cagcccgacc gctgcgcctt atccggtaac tatcgtcttg agtccaaccc ggtaagacac      5640
gacttatcgc cactggcagc agccactggt aacaggatta gcagagcgag gtatgtaggc      5700
```

-continued

```
ggtgctacag agttcttgaa gtggtggcct aactacggct acactagaag gacagtattt    5760
ggtatctgcg ctctgctgaa gccagttacc ttcggaaaaa gagttggtag ctcttgatcc    5820
ggcaaacaaa ccaccgctgg tagcggtggt ttttttgttt gcaagcagca gattacgcgc    5880
agaaaaaaag gatctcaaga agatcctttg atcttttcta cggggtctga cgctcagtgg    5940
aacgaaaact cacgttaagg gattttggtc atgagattat caaaaaggat cttcacctag    6000
atccttttaa attaaaaatg aagttttaaa tcaatctaaa gtatatatga gtaaacttgg    6060
tctgacagtt accaatgctt aatcagtgag gcacctatct cagcgatctg tctatttcgt    6120
tcatccatag ttgcctgact ccccgtcgtg tagataacta cgatacggga gggcttacca    6180
tctggcccca gtgctgcaat gataccgcga gacccacgct caccggctcc agatttatca    6240
gcaataaacc agccagccgg aagggccgag cgcagaagtg gtcctgcaac tttatccgcc    6300
tccatccagt ctattaattg ttgccgggaa gctagagtaa gtagttcgcc agttaatagt    6360
ttgcgcaacg ttgttgccat tgctacaggc atcgtggtgt cacgctcgtc gtttggtatg    6420
gcttcattca gctccggttc ccaacgatca aggcgagtta catgatcccc catgttgtgc    6480
aaaaaagcgg ttagctcctt cggtcctccg atcgttgtca agtaagtt ggccgcagtg    6540 ttatcactca tggttatggc agcactgcat aattctctta ctgtcatgcc atccgtaaga    6600
tgcttttctg tgactggtga gtactcaacc aagtcattct gagaatagtg tatgcggcga    6660
ccgagttgct cttgcccggc gtcaatacgg gataataccg cgccacatag cagaacttta    6720
aaagtgctca tcattggaaa acgttcttcg ggcgaaaac tctcaaggat cttaccgctg    6780
ttgagatcca gttcgatgta acccactcgt gcacccaact gatcttcagc atcttttact    6840
ttcaccagcg tttctgggtg agcaaaaaca ggaaggcaaa atgccgcaaa aagggaata    6900 agggcgacac ggaaatgttg aatactcata ctcttccttt ttcaatatta ttgaagcatt    6960
tatcagggtt attgtctcat gagcggatac atatttgaat gtatttagaa aaataaacaa    7020
ataggggttc cgcgcacatt tccccgaaaa gtgccacctg acgtcgacgg atcggg      7076
```

<210> SEQ ID NO 21
<211> LENGTH: 7076
<212> TYPE: DNA
<213> ORGANISM: vector

<400> SEQUENCE: 21

```
agatctcggc cgcatattaa gtgcattgtt ctcgataccg ctaagtgcat tgttctcgtt      60
agctcgatgg acaagtgcat tgttctcttg ctgaaagctc gatggacaag tgcattgttc     120
tcttgctgaa agctcgatgg acaagtgcat tgttctcttg ctgaaagctc agtacccggg     180
agtaccctcg accgccggag tataaataga ggcgcttcgt ctacggagcg acaattcaat     240
tcaaacaagc aaagtgaaca cgtcgctaag cgaaagctaa gcaaataaac aagcgcagct     300
gaacaagcta acaatctgc agtaaagtgc aagttaaagt gaatcaatta aaagtaacca     360
gcaaccaagt aaatcaactg caactactga aatctgccaa gaagtaatta ttgaatacaa     420
gaagagaact ctgaatactt tcaacaagtt accgagaaag aagaactcac acacagctag     480
cataacttcg tataatgtat gctatacgaa gttatcttaa ggaagttcct attccgaagt     540
tcctattctc tagaaagtat aggaacttcc cttaattaat tcccactagt ccagtgtggt     600
ggaattctgc agatatccag cacagtggcg gccgctcgag ccaattccgc cctctccct     660 cccccccccc taacgttact ggccgaagcc gcttggaata aggccggtgt gcgtttgtct     720
```

-continued

| | | | | |
|---|---|---|---|---|
| atatgtgatt | ttccaccata | ttgccgtctt | ttggcaatgt | gagggcccgg aaacctggcc | 780 |
| ctgtcttctt | gacgagcatt | cctagggtc | tttcccctct | cgccaaagga atgcaaggtc | 840 |
| tgttgaatgc | cgtgaaggaa | gcagttcctc | tggaagcttc | ttgaagacaa acaacgtctg | 900 |
| tagcgaccct | ttgcaggcag | cggaaccccc | cacctggcga | caggtgcctc tgcggccaaa | 960 |
| agccacgtgt | ataagataca | cctgcaaagg | cggcacaacc | ccagtgccac gttgtgagtt | 1020 |
| ggatagttgt | ggaaagagtc | aaatggctct | cctcaagcgt | attcaacaag ggctgaagg | 1080 |
| atgcccagaa | ggtaccccat | tgtatgggat | ctgatctggg | gcctcggtgc acatgcttta | 1140 |
| catgtgttta | gtcgaggtta | aaaaaacgtc | taggccccc | gaaccacggg acgtggttt | 1200 |
| tcctttgaaa | aacacgatga | taagcttgcc | acaacccgt | ctagcccggg ctcgagatct | 1260 |
| gcgatctaag | taagcttcga | atcgcgaatt | cgcccaccat | gctgctgctg ctgctgctgc | 1320 |
| tgggcctgag | gctacagctc | tccctgggca | tcatcccagt | tgaggaggag aacccggact | 1380 |
| tctggaaccg | cgaggcagcc | gaggccctgg | gtgccgccaa | gaagctgcag cctgcacaga | 1440 |
| cagccgccaa | gaacctcatc | atcttcctgg | gcgatgggat | ggggtgtct acggtgacag | 1500 |
| ctgccaggat | cctaaaaggg | cagaagaagg | acaaactggg | gcctgagata ccctggcca | 1560 |
| tggaccgctt | cccatatgtg | gctctgtcca | agacatacaa | tgtagacaaa catgtgccag | 1620 |
| acagtggagc | cacagccacg | gcctacctgt | gcggggtcaa | gggcaacttc cagaccattg | 1680 |
| gcttgagtgc | agccgcccgc | tttaaccagt | gcaacacgac | acgcggcaac gaggtcatct | 1740 |
| ccgtgatgaa | tcgggccaag | aaagcaggga | agtcagtggg | agtggtaacc accacacgag | 1800 |
| tgcagcacgc | ctcgccagcc | ggcacctacg | cccacgggt | gaaccgcaac tggtactcgg | 1860 |
| acgccgacgt | gcctgcctcg | gcccgccagg | aggggtgcca | ggacatcgct acgcagctca | 1920 |
| tctccaacat | ggacattgac | gtgatcctag | gtggaggccg | aaagtacatg tttcgcatgg | 1980 |
| gaaccccaga | ccctgagtac | ccagatgact | acagccaagg | tgggaccagg ctggacggga | 2040 |
| agaatctggt | gcaggaatgg | ctggcgaagc | gccagggtgc | ccggtatgtg tggaaccgca | 2100 |
| ctgagctcat | gcaggcttcc | ctggaccgt | ctgtgaccca | tctcatgggt ctctttgagc | 2160 |
| ctggagacat | gaaatacgag | atccaccgag | actccacact | ggacccctcc ctgatggaga | 2220 |
| tgacagaggc | tgccctgcgc | ctgctgagca | ggaaccccg | cggcttcttc ctcttcgtgg | 2280 |
| agggtggtcg | catcgaccat | ggtcatcatg | aaagcagggc | ttaccgggca ctgactgaga | 2340 |
| cgatcatgtt | cgacgacgcc | attgagaggg | cgggccagct | caccagcgag gaggacacgc | 2400 |
| tgagcctcgt | cactgccgac | cactcccacg | tcttctcctt | cggaggctac cccctgcgag | 2460 |
| ggagctccat | cttcgggctg | gcccctggca | aggccccgga | caggaaggcc tacacggtcc | 2520 |
| tcctatacgg | aaacggtcca | ggctatgtgc | tcaaggacgg | cgcccggccg atgttaccg | 2580 |
| agagcgagag | cggggagcccc | gagtatcggc | agcagtcagc | agtgccccctg gacgaagaga | 2640 |
| cccacgcagg | cgaggacgtg | gcggtgttcg | cgcgcggccc | gcaggcgcac ctggttcacg | 2700 |
| gcgtgcagga | gcagaccttc | atagcgcacg | tcatggcctt | cgccgcctgc ctggagccct | 2760 |
| acaccgcctg | cgacctggcg | ccccccgccg | gcaccaccga | cgccgcgcac ccgggttact | 2820 |
| ctagagtcgg | ggcggccggc | cgcttcgagc | agacatctcc | cgggaatccg cggctgcagg | 2880 |
| tcgacgaaca | aaaactcatc | tcagaagagg | atctgaatgc | tgtgggccag gacacgcagg | 2940 |
| aggtcatcgt | ggtgccacac | tccttgccct | ttaaggtggt | ggtgatctca gccatcctgg | 3000 |
| ccctggtggt | gctcaccatc | atctccctta | tcatcctcat | catgctttgg cagaagaagc | 3060 |
| cacgttaggc | ggccgctcga | gatcagctag | agggcccgtt | taaacccgct gatcagcctc | 3120 |

```
gactgtgcct tctagttgcc agccatctgt tgtttgcccc tccccgtgc cttccttgac      3180 cctggaaggt gccactccca ctgtcctttc ctaataaaat gaggaaattg catcgcattg      3240
tctgagtagg tgtcattcta ttctgggggg tgggtgggg caggacagca aggggagga      3300 ttgggaagac aatagcaggc atgcataact tcgtataatg tatgctatac gaagttatta     3360
attctgtgga atgtgtgtca gttagggtgt ggaaagtccc caggctcccc aggcaggcag     3420
aagtatgcaa agcatgcatc tcaattagtc agcaaccagg tgtggaaagt ccccaggctc     3480
cccagcaggc agaagtatgc aaagcatgca tctcaattag tcagcaacca tagtcccgcc     3540
cctaactccg cccatcccgc ccctaactcc gcccagttcc gcccattctc cgccccatgg     3600
ctgactaatt ttttttattt atgcagaggc cgaggccgcc tctgcctctg agctattcca     3660
gaagtagtga ggaggctttt ttggaggcct aggcttttgc aaaaagctcc cgggagcttg     3720
tatatccatt ttcggatctg atcaagagac aggatgagga tcgtttcgca tgattgaaca     3780
agatggattg cacgcaggtt ctccggccgc ttgggtggag aggctattcg gctatgactg     3840
ggcacaacag acaatcggct gctctgatgc cgccgtgttc cggctgtcag cgcaggggcg     3900
cccggttctt tttgtcaaga ccgacctgtc cggtgccctg aatgaactgc aggacgaggc     3960
agcgcggcta tcgtggctgg ccacgacggg cgttccttgc gcagctgtgc tcgacgttgt     4020
cactgaagcg ggaagggact ggctgctatt gggcgaagtg ccggggcagg atctcctgtc     4080
atctcacctt gctcctgccg agaaagtatc catcatggct gatgcaatgc ggcggctgca     4140
tacgcttgat ccggctacct gcccattcga ccaccaagcg aaacatcgca tcgagcgagc     4200
acgtactcgg atgaagccg gtcttgtcga tcaggatgat ctggacgaag agcatcaggg     4260
gctcgcgcca gccgaactgt tcgccaggct caaggcgcgc atgcccgacg gcgaggatct     4320
cgtcgtgacc catggcgatg cctgcttgcc gaatatcatg gtggaaaatg gccgcttttc     4380
tggattcatc gactgtggcc ggctgggtgt ggcggaccgc tatcaggaca tagcgttggc     4440
tacccgtgat attgctgaag agcttggcgg cgaatgggct gaccgcttcc tcgtgcttta     4500
cggtatcgcc gctcccgatt cgcagcgcat cgccttctat cgccttcttg acgagttctt     4560
ctgagcggga ctctggggtt cgaaatgacc gaccaagcga cgcccaacct gccatcacga     4620
gatttcgatt ccaccgccgc cttctatgaa aggttgggct tcggaatcgt tttccgggac     4680
gccggctgga tgatcctcca gcgcggggat ctcatgctgg agttcttcgc ccaccccaac     4740
ttgtttattg cagcttataa tggttacaaa taaagcaata gcatcacaaa tttcacaaat     4800
aaagcatttt tttcactgca ttctagttgt ggtttgtcca aactcatcaa tgtatcttat     4860
catgtctgta taccgtcgac ctctagctag agcttggcgt aatcatggtc atagctgttt     4920
cctgtgtgaa attgttatcc gctcacaatt ccacacaaca tacgagccgg aagcataaag     4980
tgtaaagcct ggggtgccta atgagtgagc taactcacat taattgcgtt gcgctcactg     5040
cccgctttcc agtcgggaaa cctgtcgtgc cagctgcatt aatgaatcgg ccaacgcgcg     5100
gggagaggcg gtttgcgtat tgggcgctct tccgcttcct cgctcactga ctcgctgcgc     5160
tcggtcgttc ggctgcggcg agcggtatca gctcactcaa aggcggtaat acggttatcc     5220
acagaatcag gggataacgc aggaaagaac atgtgagcaa aaggccagca aaaggccagg     5280
aaccgtaaaa aggccgcgtt gctggcgttt ttccataggc tccgcccccc tgacgagcat     5340
cacaaaaatc gacgctcaag tcagaggtgg cgaaacccga caggactata aagataccag     5400
gcgtttcccc ctggaagctc cctcgtgcgc tctcctgttc cgaccctgcc gcttaccgga     5460
```

-continued

| | |
|---|---|
| tacctgtccg cctttctccc ttcgggaagc gtggcgcttt ctcaatgctc acgctgtagg | 5520 |
| tatctcagtt cggtgtaggt cgttcgctcc aagctgggct gtgtgcacga accccccgtt | 5580 |
| cagcccgacc gctgcgcctt atccggtaac tatcgtcttg agtccaaccc ggtaagacac | 5640 |
| gacttatcgc cactggcagc agccactggt aacaggatta gcagagcgag gtatgtaggc | 5700 |
| ggtgctacag agttcttgaa gtggtggcct aactacggct acactagaag gacagtattt | 5760 |
| ggtatctgcg ctctgctgaa gccagttacc ttcggaaaaa gagttggtag ctcttgatcc | 5820 |
| ggcaaacaaa ccaccgctgg tagcggtggt ttttttgttt gcaagcagca gattacgcgc | 5880 |
| agaaaaaaag gatctcaaga agatcctttg atcttttcta cggggtctga cgctcagtgg | 5940 |
| aacgaaaact cacgttaagg gattttggtc atgagattat caaaaaggat cttcacctag | 6000 |
| atccttttaa attaaaaatg aagttttaaa tcaatctaaa gtatatatga gtaaacttgg | 6060 |
| tctgacagtt accaatgctt aatcagtgag gcacctatct cagcgatctg tctatttcgt | 6120 |
| tcatccatag ttgcctgact ccccgtcgtg tagataacta cgatacggga gggcttacca | 6180 |
| tctggcccca gtgctgcaat gataccgcga gacccacgct caccggctcc agatttatca | 6240 |
| gcaataaacc agccagccgg aagggccgag cgcagaagtg gtcctgcaac tttatccgcc | 6300 |
| tccatccagt ctattaattg ttgccgggaa gctagagtaa gtagttcgcc agttaatagt | 6360 |
| ttgcgcaacg ttgttgccat tgctacaggc atcgtggtgt cacgctcgtc gtttggtatg | 6420 |
| gcttcattca gctccggttc ccaacgatca aggcgagtta catgatcccc catgttgtgc | 6480 |
| aaaaaagcgg ttagctcctt cggtcctccg atcgttgtca agtaagtt ggccgcagtg | 6540 |
| ttatcactca tggttatggc agcactgcat aattctctta ctgtcatgcc atccgtaaga | 6600 |
| tgcttttctg tgactggtga gtactcaacc aagtcattct gagaatagtg tatgcggcga | 6660 |
| ccgagttgct cttgcccggc gtcaatacgg gataataccg cgccacatag cagaacttta | 6720 |
| aaagtgctca tcattggaaa acgttcttcg ggcgaaaac tctcaaggat cttaccgctg | 6780 |
| ttgagatcca gttcgatgta acccactcgt gcacccaact gatcttcagc atcttttact | 6840 |
| ttcaccagcg tttctgggtg agcaaaaaca ggaaggcaaa atgccgcaaa aagggaata | 6900 |
| agggcgacac ggaaatgttg aatactcata ctcttccttt ttcaatatta ttgaagcatt | 6960 |
| tatcagggtt attgtctcat gagcggatac atatttgaat gtatttagaa aaataaacaa | 7020 |
| ataggggttc cgcgcacatt tccccgaaaa gtgccacctg acgtcgacgg atcggg | 7076 |

<210> SEQ ID NO 22
<211> LENGTH: 7092
<212> TYPE: DNA
<213> ORGANISM: vector

<400> SEQUENCE: 22

| | |
|---|---|
| agatctcggc cgcatattaa gtgcattgtt ctcgataccg ctaagtgcat tgttctcgtt | 60 |
| agctcgatgg acaagtgcat tgttctcttg ctgaaagctc gatggacaag tgcattgttc | 120 |
| tcttgctgaa agctcgatgg acaagtgcat tgttctcttg ctgaaagctc agtacccggg | 180 |
| agtaccctcg accgccggag tataaataga ggcgcttcgt ctacggagcg acaattcaat | 240 |
| tcaaacaagc aaagtgaaca cgtcgctaag cgaaagctaa gcaaataaac aagcgcagct | 300 |
| gaacaagcta acaatctgc agtaaagtgc aagttaaagt gaatcaatta aaagtaacca | 360 |
| gcaaccaagt aaatcaactg caactactga aatctgccaa gaagtaatta ttgaatacaa | 420 |
| gaagagaact ctgaatactt tcaacaagtt accgagaaag aagaactcac acacagctag | 480 |
| cataacttcg tataatgtat gctatacgaa gttatcttaa ggaagttcct attccgaagt | 540 |

```
tcctattctc tagaaagtat aggaacttcc cttaattaat tcccactagt ccagtgtggt    600
ggaattctgc agatatccag cacagtggcg gccgctcgag ccaattccgc ccctctccct    660 ccccccccc  taacgttact ggccgaagcc gcttggaata aggccggtgt gcgtttgtct    720
atatgtgatt ttccaccata ttgccgtctt ttggcaatgt gagggccgg  aaacctggcc    780 ctgtcttctt gacgagcatt cctaggggtc tttcccctct cgccaaagga atgcaaggtc    840
tgttgaatgt cgtgaaggaa gcagttcctc tggaagcttc ttgaagacaa acaacgtctg    900
tagcgaccct ttgcaggcag cggaaccccc cacctggcga caggtgcctc tgcggccaaa    960
agccacgtgt ataagataca cctgcaaagg cggcacaacc ccagtgccac gttgtgagtt   1020
ggatagttgt ggaaagagtc aaatggctct cctcaagcgt attcaacaag gggctgaagg   1080
atgcccagaa ggtaccccat tgtatgggat ctgatctggg gcctcggtgc acatgcttta   1140
catgtgttta gtcgaggtta aaaaaacgtc taggcccccc gaaccacggg gacgtggttt   1200
tcctttgaaa aacacgatga taagcttgcc acaacccggt ctagcccggg ctcgagatct   1260
gcgatctaag taagcttcga atcgcgaatt cgcccaccat gctgctgctg ctgctgctgc   1320
tgggcctgag gctacagctc tccctgggca tcatcccagt tgaggaggag aacccggact   1380
tctggaaccg cgaggcagcc gaggccctgg gtgccgccaa gaagctgcag cctgcacaga   1440
cagccgccaa gaacctcatc atcttcctgg gcgatgggat ggggtgtctc acggtgacag   1500
ctgccaggat cctaaaaggg cagaagaagg acaaactggg gcctgagata cccctggcca   1560
tggaccgctt cccatatgtg gctctgtcca agacatacaa tgtagacaaa catgtgccag   1620
acagtggagc cacagccacg gcctaccgtg cggggtcaa  gggcaacttc cagaccattg   1680
gcttgagtgc agccgcccgc tttaaccagt gcaacacgac acgcggcaac gaggtcatct   1740
ccgtgatgaa tcgggccaag aaagcaggga agtcagtggg agtggtaacc accacacgag   1800
tgcagcacgc ctcgccagcc ggcacctacg cccacacggt gaaccgcaac tggtactcgg   1860
acgccgacgt gcctgcctcg gcccgccagg aggggtgcca ggacatcgct acgcagctca   1920
tctccaacat ggacattgac gtgatcctag gtggaggccg aaagtacatg tttcgcatgg   1980
gaaccccaga ccctgagtac ccagatgact acagccaagg tggaccagg  ctggacggga   2040 agaatctggt gcaggaatgg ctggcgaagc gccagggtgc ccggtatgtg tggaaccgca   2100
ctgagctcat gcaggcttcc ctggaccgt  ctgtgaccca tctcatgggt ctctttgagc   2160
ctggagacat gaaatacgag atccaccgag actccacact ggaccctcc  ctgatggaga   2220 tgacagaggc tgccctgcgc ctgctgagca ggaaccccg  cggcttcttc ctcttcgtgg   2280
agggtggtcg catcgaccat ggtcatcatg aaagcagggc ttaccgggca ctgactgaga   2340
cgatcatgtt cgacgacgcc attgagaggg cgggccagct caccagcgag gaggacacgc   2400
tgagcctcgt cactgccgac cactcccacg tcttctcctt cggaggctac ccctgcgag   2460 ggagctccat cttcgggctg gcccctggca aggcccggga caggaaggcc tacacggtcc   2520
tcctatacgg aaacggtcca ggctatgtgc tcaaggacgg cgcccggccg gatgttaccg   2580
agagcgagag cggagccccc gagtatcggc agcagtcagc agtgcccctg acgaagaga   2640 cccacgcagg cgaggacgtg gcggtgttcg cgcgcgcccc gcaggcgcac ctggttcacg   2700
gcgtgcagga gcagaccttc atagcgcacg tcatggcctt cgccgcctgc ctggagccct   2760
acaccgcctg cgacctggcg cccccgccg  gcaccaccga cgccgcgcac ccgggttact   2820
ctagagtcgg ggcggccggc cgcttcgagc agacatctcc cgggaatccg cggctgcagg   2880
```

-continued

| | |
|---|---|
| tcgacgaaca aaaactcatc tcagaagagg atctgaatgc tgtgggccag gacacgcagg | 2940 |
| aggtcatcgt ggtgccacac tccttgccct ttaaggtggt ggtgatctca gccatcctgg | 3000 |
| ccctggtggt gctcaccatc atctccctta tcatcctcat catgctttgg cagaagaagc | 3060 |
| cacgttaggc ggccgctcga gatcagctag agggcccgtt taaacccgct gatcagcctc | 3120 |
| gactgtgcct tctagttgcc agccatctgt tgtttgcccc tcccccgtgc cttccttgac | 3180 |
| cctggaaggt gccactccca ctgtcctttc ctaataaaat gaggaaattg catcgcattg | 3240 |
| tctgagtagg tgtcattcta ttctgggggg tggggtgggg caggacagca agggggagga | 3300 |
| ttgggaagac aatagcaggc atgcgaagtt cctattccga agttcctatt ctctagaaag | 3360 |
| tataggaact tcattaattc tgtggaatgt gtgtcagtta gggtgtggaa agtccccagg | 3420 |
| ctccccaggc aggcagaagt atgcaaagca tgcatctcaa ttagtcagca accaggtgtg | 3480 |
| gaaagtcccc aggctcccca gcaggcagaa gtatgcaaag catgcatctc aattagtcag | 3540 |
| caaccatagt cccgcccta actccgccca tcccgcccct aactccgccc agttccgccc | 3600 |
| attctccgcc ccatggctga ctaatttttt ttatttatgc agaggccgag gccgcctctg | 3660 |
| cctctgagct attccagaag tagtgaggag gcttttttgg aggcctaggc ttttgcaaaa | 3720 |
| agctcccggg agcttgtata tccattttcg gatctgatca agagacagga tgaggatcgt | 3780 |
| ttcgcatgat tgaacaagat ggattgcacg caggttctcc ggccgcttgg gtggagaggc | 3840 |
| tattcggcta tgactggca caacagacaa tcggctgctc tgatgccgcc gtgttccggc | 3900 |
| tgtcagcgca ggggcgcccg gttcttttg tcaagaccga cctgtccggt gccctgaatg | 3960 |
| aactgcagga cgaggcagcg cggctatcgt ggctggccac gacgggcgtt ccttgcgcag | 4020 |
| ctgtgctcga cgttgtcact gaagcgggaa gggactggct gctattgggc gaagtgccgg | 4080 |
| ggcaggatct cctgtcatct caccttgctc ctgccgagaa agtatccatc atggctgatg | 4140 |
| caatgcggcg gctgcatacg cttgatccgg ctacctgccc attcgaccac caagcgaaac | 4200 |
| atcgcatcga gcgagcacgt actcggatgg aagccggtct tgtcgatcag gatgatctgg | 4260 |
| acgaagagca tcaggggctc gcgccagccg aactgttcgc caggctcaag gcgcgcatgc | 4320 |
| ccgacggcga ggatctcgtc gtgacccatg gcgatgcctg cttgccgaat atcatggtgg | 4380 |
| aaaatggccg cttttctgga ttcatcgact gtggccggct gggtgtggcg gaccgctatc | 4440 |
| aggacatagc gttggctacc cgtgatattg ctgaagagct tggcggcgaa tgggctgacc | 4500 |
| gcttcctcgt gctttacggt atcgccgctc ccgattcgca gcgcatcgcc ttctatcgcc | 4560 |
| ttcttgacga gttcttctga gcgggactct ggggttcgaa atgaccgacc aagcgacgcc | 4620 |
| caacctgcca tcacgagatt tcgattccac cgccgccttc tatgaaaggt tgggcttcgg | 4680 |
| aatcgttttc cgggacgccg gctggatgat cctccagcgc ggggatctca tgctggagtt | 4740 |
| cttcgcccac cccaacttgt ttattgcagc ttataatggt tacaaataaa gcaatagcat | 4800 |
| cacaaatttc acaaataaag cattttttc actgcattct agttgtggtt tgtccaaact | 4860 |
| catcaatgta tcttatcatg tctgtatacc gtcgacctct agctagagct tggcgtaatc | 4920 |
| atggtcatag ctgtttcctg tgtgaaattg ttatccgctc acaattccac acaacatacg | 4980 |
| agccggaagc ataaagtgta aagcctgggg tgcctaatga gtgagctaac tcacattaat | 5040 |
| tgcgttgcgc tcactgcccg ctttccagtc gggaaacctg tcgtgccagc tgcattaatg | 5100 |
| aatcggccaa cgcgcgggga gaggcggttt gcgtattggg cgctcttccg cttcctcgct | 5160 |
| cactgactcg ctgcgctcgg tcgttcggct gcggcgagcg gtatcagctc actcaaaggc | 5220 |
| ggtaatacgg ttatccacag aatcagggga taacgcagga agaacatgtg agcaaaagg | 5280 |

```
ccagcaaaag gccaggaacc gtaaaaaggc cgcgttgctg gcgttttcc ataggctccg    5340
cccccctgac gagcatcaca aaaatcgacg ctcaagtcag aggtggcgaa acccgacagg   5400
actataaaga taccaggcgt ttccccctgg aagctccctc gtgcgctctc ctgttccgac   5460
cctgccgctt accggatacc tgtccgcctt tctcccttcg ggaagcgtgg cgctttctca   5520
atgctcacgc tgtaggtatc tcagttcggt gtaggtcgtt cgctccaagc tgggctgtgt   5580
gcacgaaccc cccgttcagc ccgaccgctg cgccttatcc ggtaactatc gtcttgagtc   5640
caacccggta agacacgact tatcgccact ggcagcagcc actggtaaca ggattagcag   5700
agcgaggtat gtaggcggtg ctacagagtt cttgaagtgg tggcctaact acggctacac   5760
tagaaggaca gtatttggta tctgcgctct gctgaagcca gttaccttcg aaaaagagt    5820
tggtagctct tgatccggca acaaaccac cgctggtagc ggtggttttt ttgtttgcaa    5880
gcagcagatt acgcgcagaa aaaaggatc tcaagaagat cctttgatct tttctacggg    5940
gtctgacgct cagtggaacg aaaactcacg ttaagggatt ttggtcatga gattatcaaa   6000
aaggatcttc acctagatcc ttttaaatta aaaatgaagt tttaaatcaa tctaaagtat   6060
atatgagtaa acttggtctg acagttacca atgcttaatc agtgaggcac ctatctcagc   6120
gatctgtcta tttcgttcat ccatagttgc ctgactcccc gtcgtgtaga taactacgat   6180
acgggagggc ttaccatctg gccccagtgc tgcaatgata ccgcgagacc cacgctcacc   6240
ggctccagat ttatcagcaa taaaccagcc agccggaagg gccgagcgca gaagtggtcc   6300
tgcaacttta tccgcctcca tccagtctat taattgttgc cgggaagcta gagtaagtag   6360
ttcgccagtt aatagtttgc gcaacgttgt tgccattgct acaggcatcg tggtgtcacg   6420
ctcgtcgttt ggtatggctt cattcagctc cggttcccaa cgatcaaggc gagttacatg   6480
atcccccatg ttgtgcaaaa aagcggttag ctccttcggt cctccgatcg ttgtcagaag   6540
taagttggcc gcagtgttat cactcatggt tatggcagca ctgcataatt ctcttactgt   6600
catgccatcc gtaagatgct tttctgtgac tggtgagtac tcaaccaagt cattctgaga   6660
atagtgtatg cggcgaccga gttgctcttg cccggcgtca atacgggata taccgcgcc   6720
acatagcaga actttaaaag tgctcatcat tggaaaacgt tcttcgggc gaaaactctc    6780
aaggatctta ccgctgttga tccagttc gatgtaaccc actcgtgcac ccaactgatc    6840
ttcagcatct tttactttca ccagcgtttc tgggtgagca aaaacaggaa ggcaaaatgc   6900
cgcaaaaaag ggaataaggg cgacacggaa atgttgaata ctcatactct ccttttttca   6960
atattattga agcatttatc agggttattg tctcatgagc ggatacatat ttgaatgtat   7020
ttagaaaaat aaacaaatag gggttccgcg cacatttccc cgaaaagtgc cacctgacgt   7080
cgacggatcg gg                                                       7092
```

<210> SEQ ID NO 23
<211> LENGTH: 4491
<212> TYPE: DNA
<213> ORGANISM: vector

<400> SEQUENCE: 23

```
ctcgagaaat cataaaaaat ttatttgctt tgtgagcgga taacaattat aatagattca     60
attgtgagcg gataacaatt tcacacagaa ttcattaaag aggagaaatt aactatgaga    120
ggatcgcatc accatcacca tcacggatct tatggtcgca aaaacgccg tcagcgccgt    180
cgtggctcca atttactgac cgtacaccaa aatttgcctg cattaccggt cgatgcaacg    240
```

-continued

| | |
|---|---|
| agtgatgagg ttcgcaagaa cctgatggac atgttcaggg atcgccaggc gttttctgag | 300 |
| catacctgga aaatgcttct gtccgtttgc cggtcgtggg cggcatggtg caagttgaat | 360 |
| aaccggaaat ggtttcccgc agaacctgaa gatgttcgcg attatcttct atatcttcag | 420 |
| gcgcgcggtc tggcagtaaa aactatccag caacatttgg gccagctaaa catgcttcat | 480 |
| cgtcggtccg ggctgccacg accaagtgac agcaatgctg tttcactggt tatgcggcgg | 540 |
| atccgaaaag aaaacgttga tgccggtgaa cgtgcaaaac aggctctagc gttcgaacgc | 600 |
| actgatttcg accaggttcg ttcactcatg gaaatagcg atcgctgcca ggatatacgt | 660 |
| aatctggcat ttctggggat tgcttataac accctgttac gtatagccga aattgccagg | 720 |
| atcagggtta aagatatctc acgtactgac ggtgggagaa tgttaatcca tattggcaga | 780 |
| acgaaaacgc tggttagcac cgcaggtgta gagaaggcac ttagcctggg ggtaactaaa | 840 |
| ctggtcgagc gatggatttc cgtctctggt gtagctgatg atccgaataa ctacctgttt | 900 |
| tgccgggtca gaaaaaatgg tgttgccgcg ccatctgcca ccagccagct atcaactcgc | 960 |
| gccctggaag ggattttga agcaactcat cgattgattt acggcgctaa ggatgactct | 1020 |
| ggtcagagat acctggcctg gtctggacac agtgcccgtg tcggagccgc gcgagatatg | 1080 |
| gcccgcgctg gagtttcaat accggagatc atgcaagctg gtggctggac caatgtaaat | 1140 |
| attgtcatga actatatccg taacctggat agtgaaacag gggcaatggt gcgcctgctg | 1200 |
| gaagatggcg attagaagct taattagctg agcttggact cctgttgata gatccagtaa | 1260 |
| tgacctcaga actccatctg gatttgttca gaacgctcgg ttgccgccgg cgttttttta | 1320 |
| ttggtgagaa tccaagctag cttggcgaga ttttcaggag ctaaggaagc taaaatggag | 1380 |
| aaaaaaatca ctggatatac caccgttgat atatcccaat ggcatcgtaa agaacatttt | 1440 |
| gaggcatttc agtcagttgc tcaatgtacc tataaccaga ccgttcagct ggatattacg | 1500 |
| gcctttttaa agaccgtaaa gaaaaataag cacaagtttt atccggcctt tattcacatt | 1560 |
| cttgcccgcc tgatgaatgc tcatccggaa tttcgtatgg caatgaaaga cggtgagctg | 1620 |
| gtgatatggg atagtgttca cccttgttac accgttttcc atgagcaaac tgaaacgttt | 1680 |
| tcatcgctct ggagtgaata ccacgacgat ttccggcagt ttctacacat atattcgcaa | 1740 |
| gatgtggcgt gttacggtga aaacctggcc tatttcccta aagggtttat tgagaatatg | 1800 |
| ttttttcgtct cagccaatcc ctgggtgagt ttcaccagtt ttgatttaaa cgtggccaat | 1860 |
| atggacaact tcttcgcccc cgttttcacc atgggcaaat attatacgca aggcgacaag | 1920 |
| gtgctgatgc cgctggcgat tcaggttcat catgccgtct gtgatggctt ccatgtcggc | 1980 |
| agaatgctta atgaattaca acagtactgc gatgagtggc agggcgggc gtaattttt | 2040 |
| taaggcagtt attggtgccc ttaaacgcct ggggtaatga ctctctagct tgaggcatca | 2100 |
| aataaaacga aaggctcagt cgaaagactg ggcctttcgt tttatctgtt gtttgtcggt | 2160 |
| gaacgctctc ctgagtagga caaatccgcc gctctagagc tgcctcgcgc gtttcggtga | 2220 |
| tgacggtgaa aacctctgac acatgcagct cccggagacg tcacagctt gtctgtaagc | 2280 |
| ggatgccggg agcagacaag cccgtcaggg cgcgtcagcg ggtgttggcg ggtgtcgggg | 2340 |
| cgcagccatg acccagtcac gtagcgatag cggagtgtat actggcttaa ctatgcggca | 2400 |
| tcagagcaga ttgtactgag agtgcaccat atgcggtgtg aaataccgca cagatgcgta | 2460 |
| aggagaaaat accgcatcag cgctcttcc gcttcctcgc tcactgactc gctgcgctcg | 2520 |
| gtctgtcggc tgcggcgagc ggtatcagct cactcaaagg cggtaatacg gttatccaca | 2580 |
| gaatcagggg ataacgcagg aaagaacatg tgagcaaaag gccagcaaaa ggccaggaac | 2640 |

```
cgtaaaaagg ccgcgttgct ggcgttttc cataggctcc gcccctga cgagcatcac      2700 aaaaatcgac gctcaagtca gaggtggcga acccgacag gactataaag ataccaggcg     2760
tttccccctg gaagctccct cgtgcgctct cctgttccga ccctgccgct taccggatac    2820
ctgtccgcct ttctcccttc gggaagcgtg gcgctttctc aatgctcacg ctgtaggtat    2880
ctcagttcgg tgtaggtcgt tcgctccaag ctgggctgtg tgcacgaacc ccccgttcag    2940
cccgaccgct gcgccttatc cggtaactat cgtcttgagt ccaacccggt aagacacgac    3000
ttatcgccac tggcagcagc cactggtaac aggattagca gagcgaggta tgtaggcggt    3060
gctacagagt tcttgaagtg gtggcctaac tacggctaca ctagaaggac agtatttggt    3120
atctgcgctc tgctgaagcc agttaccttc ggaaaaagag ttggtagctc ttgatccggc    3180
aaacaaacca ccgctggtag cggtggtttt tttgtttgca agcagcagat tacgcgcaga    3240 aaaaaggat ctcaagaaga tcctttgatc ttttctacgg ggtctgacgc tcagtggaac     3300
gaaaactcac gttaagggat tttggtcatg agattatcaa aaggatctt cacctagatc     3360 cttttaaatt aaaaatgaag ttttaaatca atctaaagta tatatgagta aacttggtct    3420
gacagttacc aatgcttaat cagtgaggca cctatctcag cgatctgtct atttcgttca    3480
tccatagctg cctgactccc cgtcgtgtag ataactacga tacgggaggg cttaccatct    3540
ggccccagtg ctgcaatgat accgcgagac ccacgctcac cggctccaga tttatcagca    3600
ataaaccagc cagccggaag ggccgagcgc agaagtggtc ctgcaacttt atccgcctcc    3660
atccagtcta ttaattgttg ccgggaagct agagtaagta gttcgccagt taatagtttg    3720
cgcaacgttg ttgccattgc tacaggcatc gtggtgtcac gctcgtcgtt tggtatggct    3780
tcattcagct ccggttccca acgatcaagg cgagttacat gatcccccat gttgtgcaaa    3840
aaagcggtta gctccttcgg tcctccgatc gttgtcagaa gtaagttggc cgcagtgtta    3900
tcactcatgg ttatggcagc actgcataat tctcttactg tcatgccatc cgtaagatgc    3960
ttttctgtga ctggtgagta ctcaaccaag tcattctgag aatagtgtat gcggcgaccg    4020
agttgctctt gcccggcgtc aatacgggat aataccgcgc cacatagcag aactttaaaa    4080
gtgctcatca ttggaaaacg ttcttcgggg cgaaaactct caaggatctt accgctgttg    4140
agatccagtt cgatgtaacc cactcgtgca cccaactgat cttcagcatc ttttactttc    4200
accagcgttt ctgggtgagc aaaaacagga aggcaaaatg ccgcaaaaaa gggaataagg    4260
gcgacacgga aatgttgaat actcatactc ttccttttc aatattattg aagcatttat     4320
cagggttatt gtctcatgag cggatacata tttgaatgta tttagaaaaa taaacaaata    4380
ggggttccgc gcacatttcc ccgaaaagtg ccacctgacg tctaagaaac cattattatc    4440
atgacattaa cctataaaaa taggcgtatc acgaggccct ttcgtcttca c             4491
```

<210> SEQ ID NO 24
<211> LENGTH: 4755
<212> TYPE: DNA
<213> ORGANISM: vector

<400> SEQUENCE: 24

```
ctcgagaaat cataaaaaat ttatttgctt tgtgagcgga taacaattat aatagattca      60
attgtgagcg gataacaatt tcacacagaa ttcattaaag aggagaaatt aactatgaga    120
ggatcgcatc accatcacca tcacggatct tatggtcgca aaaacgccg tcagcgccgt      180 cgtggcccac aatttgatat attatgtaaa acaccaccta aggtgcttgt tcgtcagttt    240
```

-continued

| | | |
|---|---|---|
| gtggaaaggt tgaaagacc ttcaggtgag aaaatagcat tatgtgctgc tgaactaacc | 300 |
| tatttatgtt ggatgattac acataacgga acagcaatca agagagccac attcatgagc | 360 |
| tataatacta tcataagcaa ttcgctgagt ttggatattg tcaacaagtc actgcagttt | 420 |
| aaatacaaga cgcaaaaagc aacaattctg gaagcctcat taaagaaatt gattcctgct | 480 |
| tgggaattta caattattcc ttactatgga caaaaacatc aatctgatat cactgatatt | 540 |
| gtaagtagtt tgcaattaca gttcgaatca tcggaagaag cagataaggg aaatagccac | 600 |
| agtaaaaaaa tgcttaaagc acttctaagt gagggtgaaa gcatctggga gatcactgag | 660 |
| aaaatactaa attcgtttga gtatacttcg agatttacaa aaacaaaaac tttataccaa | 720 |
| ttcctcttcc tagctacttt catcaattgt ggaagattca gcgatattaa gaacgttgat | 780 |
| ccgaaatcat ttaaattagt ccaaaataag tatctgggag taataatcca gtgtttagtg | 840 |
| acagagacaa agacaagcgt tagtaggcac atatacttct ttagcgcaag ggtaggatc | 900 |
| gatccacttg tatatttgga tgaatttttg aggaattctg aaccagtcct aaaacgagta | 960 |
| aataggaccg gcaattcttc aagcaacaag caggaatacc aattattaaa agataactta | 1020 |
| gtcagatcgt acaacaaagc tttgaagaaa aatgcgcctt attcaatctt tgctataaaa | 1080 |
| aatggcccaa aatctcacat tggaagacat ttgatgacct catttctttc aatgaagggc | 1140 |
| ctaacggagt tgactaatgt tgtgggaaat tggagcgata agcgtgcttc tgccgtggcc | 1200 |
| aggacaacgt atactcatca gataacagca atacctgatc actacttcgc actagtttct | 1260 |
| cggtactatg catatgatcc aatatcaaag gaaatgatag cattgaagga tgagactaat | 1320 |
| ccaattgagg agtggcagca tatagaacag ctaagggta gtgctgaagg aagcatacga | 1380 |
| taccccgcat ggaatgggat aatatcacag gaggtactag actacctttc atcctacata | 1440 |
| aatagacgca tataaggtac cccgggtcga cctgcagcca agcttaatta gctgagcttg | 1500 |
| gactcctgtt gatagatcca gtaatgacct cagaactcca tctggatttg ttcagaacgc | 1560 |
| tcggttgccg ccgggcgttt tttattggtg agaatccaag ctagcttggc gagattttca | 1620 |
| ggagctaagg aagctaaaat ggagaaaaaa atcactggat ataccaccgt tgatatatcc | 1680 |
| caatggcatc gtaaagaaca ttttgaggca tttcagtcag ttgctcaatg tacctataac | 1740 |
| cagaccgttc agctggatat tacggccttt ttaaagaccg taaagaaaaa taagcacaag | 1800 |
| ttttatccgg cctttattca cattcttgcc cgcctgatga atgctcatcc ggaatttcgt | 1860 |
| atggcaatga agacggtga gctggtgata tgggatagtg ttcacccttg ttacaccgtt | 1920 |
| ttccatgagc aaactgaaac gttttcatcg ctctggagtg aataccacga cgatttccgg | 1980 |
| cagtttctac acatatattc gcaagatgtg gcgtgttacg gtgaaaacct ggcctatttc | 2040 |
| cctaaagggt ttattgagaa tatgtttttc gtctcagcca atccctgggt gagtttcacc | 2100 |
| agttttgatt taaacgtggc caatatggac aacttcttcg ccccegtttt caccatgggc | 2160 |
| aaatattata cgcaaggcga caaggtgctg atgccgctgg cgattcaggt tcatcatgcc | 2220 |
| gtctgtgatg gcttccatgt cggcagaatg cttaatgaat acaacagta ctgcgatgag | 2280 |
| tggcagggcg gggcgtaatt tttttaaggc agttattggt gcccttaaac gcctgggta | 2340 |
| atgactctct agcttgaggc atcaaataaa acgaaaggct cagtcgaaag actgggcctt | 2400 |
| tcgttttatc tgttgtttgt cggtgaacgc tctcctgagt aggacaaatc cgccgctcta | 2460 |
| gagctgcctc gcgcgtttcg gtgatgacgg tgaaaacctc tgacacatgc agctcccgga | 2520 |
| gacggtcaca gcttgtctgt aagcggatgc cgggagcaga caagcccgtc agggcgcgtc | 2580 |
| agcgggtgtt ggcgggtgtc ggggcgcagc catgacccag tcacgtagcg atagcggagt | 2640 |

```
gtatactggc ttaactatgc ggcatcagag cagattgtac tgagagtgca ccatatgcgg    2700
tgtgaaatac cgcacagatg cgtaaggaga aaataccgca tcaggcgctc ttccgcttcc    2760
tcgctcactg actcgctgcg ctcggtctgt cggctgcggc gagcggtatc agctcactca    2820
aaggcggtaa tacggttatc cacagaatca ggggataacg caggaaagaa catgtgagca    2880
aaaggccagc aaaaggccag gaaccgtaaa aaggccgcgt tgctggcgtt tttccatagg    2940
ctccgccccc ctgacgagca tcacaaaaat cgacgctcaa gtcagaggtg gcgaaacccg    3000
acaggactat aaagatacca ggcgtttccc cctggaagct ccctcgtgcg ctctcctgtt    3060
ccgaccctgc cgcttaccgg atacctgtcc gcctttctcc cttcgggaag cgtggcgctt    3120
tctcaatgct cacgctgtag gtatctcagt tcggtgtagg tcgttcgctc caagctgggc    3180
tgtgtgcacg aaccccccgt tcagcccgac cgctgcgcct tatccggtaa ctatcgtctt    3240
gagtccaacc cggtaagaca cgacttatcg ccactggcag cagccactgg taacaggatt    3300
agcagagcga ggtatgtagg cggtgctaca gagttcttga agtggtggcc taactacggc    3360
tacactagaa ggacagtatt tggtatctgc gctctgctga gccagttac  cttcggaaaa    3420 agagttggta gctcttgatc cggcaaacaa accaccgctg gtagcggtgg tttttttgtt    3480
tgcaagcagc agattacgcg cagaaaaaaa ggatctcaag aagatccttt gatcttttct    3540
acggggtctg acgctcagtg gaacgaaaac tcacgttaag ggattttggt catgagatta    3600
tcaaaaagga tcttcaccta gatccttttta aattaaaaat gaagttttaa atcaatctaa    3660
agtatatatg agtaaacttg gtctgacagt taccaatgct taatcagtga ggcacctatc    3720
tcagcgatct gtctatttcg ttcatccata gctgcctgac tccccgtcgt gtagataact    3780
acgatacggg agggcttacc atctggcccc agtgctgcaa tgataccgcg agacccacgc    3840
tcaccggctc cagatttatc agcaataaac cagccagccg aagggccga gcgcagaagt    3900 ggtcctgcaa ctttatccgc ctccatccag tctattaatt gttgccggga agctagagta    3960
agtagttcgc cagttaatag tttgcgcaac gttgttgcca ttgctacagg catcgtggtg    4020
tcacgctcgt cgtttggtat ggcttcattc agctccggtt cccaacgatc aaggcgagtt    4080
acatgatccc ccatgttgtg caaaaaagcg gttagctcct tcggtcctcc gatcgttgtc    4140
agaagtaagt tggccgcagt gttatcactc atggttatgg cagcactgca taattctctt    4200
actgtcatgc catccgtaag atgcttttct gtgactggtg agtactcaac caagtcattc    4260
tgagaatagt gtatgcggcg accgagttgc tcttgcccgg cgtcaatacg ggataatacc    4320
gcgccacata gcagaacttt aaaagtgctc atcattggaa aacgttcttc ggggcgaaaa    4380
ctctcaagga tcttaccgct gttgagatcc agttcgatgt aacccactcg tgcacccaac    4440
tgatcttcag catcttttac tttcaccagc gtttctgggt gagcaaaaac aggaaggcaa    4500
aatgccgcaa aaaagggaat aagggcgaca cggaaatgtt gaatactcat actcttcctt    4560
tttcaatatt attgaagcat ttatcagggt tattgtctca tgagcggata catatttgaa    4620
tgtatttaga aaaataaaca ataggggtt ccgcgcacat ttccccgaaa agtgccacct    4680
gacgtctaag aaaccattat tatcatgaca ttaacctata aaaataggcg tatcacgagg    4740
ccctttcgtc ttcac                                                    4755

<210> SEQ ID NO 25
<211> LENGTH: 6452
<212> TYPE: DNA
<213> ORGANISM: vector
```

-continued

```
<400> SEQUENCE: 25
gacggatcgg gagatcctag cgtttaaact taaggaagtt cctattccga agttcctatt      60
ctctagaaag tataggaact tcccttaatt aattcccact agtccagtgt ggtggaattc     120
tgcagatatc cagcacagtg gcggccgctc gagccaattc cgcccctctc cctcccccc     180 ccctaacgtt actggccgaa gccgcttgga ataaggccgg tgtgcgtttg tctatatgtg     240
attttccacc atattgccgt cttttggcaa tgtgagggcc cggaaacctg ccctgtctt     300 cttgacgagc attcctaggg gtctttcccc tctcgccaaa ggaatgcaag gtctgttgaa     360
tgtcgtgaag gaagcagttc tctggaagc ttcttgaaga caaacaacgt ctgtagcgac      420
cctttgcagg cagcggaacc ccccacctgg cgacaggtgc ctctgcggcc aaaagccacg     480
tgtataagat acacctgcaa aggcggcaca accccagtgc cacgttgtga gttggatagt     540
tgtggaaaga gtcaaatggc tctcctcaag cgtattcaac aaggggctga aggatgccca     600
gaaggtaccc cattgtatgg gatctgatct ggggcctcgg tgcacatgct ttacatgtgt     660
ttagtcgagg ttaaaaaaac gtctaggccc cccgaaccac ggggacgtgg ttttccttg      720 aaaaacacga tgataagctt gccacaaccc ggtctagaat gctgctgctg ccatttcaac     780
tgttagctgt tctcttcct ggtggtaaca gtgaacatgc cttccagggg ccgacctcct      840
ttcatgttat ccagacctcg tccttacca atagtacctg gcacaaaact caaggctcag      900
gctggttgga tgatttgcag attcatggct gggatagcga ctcaggcact gccatattcc     960
tgaagccttg gtctaaaggt aactttagtg ataaggaggt tgctgagtta gaggagatat    1020
tccgagtcta catctttgga ttcgctcgag aagtacaaga cttgccggt gatttccaga     1080 tgaaataccc ctttgagatc cagggcatag caggctgtga gctacattct ggaggtgcca    1140
tagtaagctt cctgagggga gctctaggag gattggattt cctgagtgtc aagaatgctt    1200
catgtgtgcc ttccccagaa ggtggcagca gggcacagaa attctgtgca ctaatcatac    1260
aatatcaagg tatcatggaa actgtgagaa ttctcctcta tgaaacctgc cccgatatc     1320 tcttgggcgt cctcaatgca ggaaaagcag atctgcaaag acaagtgaag cctgaggcct    1380
ggctgtccag tggccccagt cctggacctg gccgtctgca gcttgtgtgc catgtctcag    1440
gattctaccc aaagcccgtg tgggtgatgt ggatgcgggg tgagcaggag cagcagggca    1500
ctcagctagg ggacatcctg cccaatgcta actggacatg gtatctccga gcaaccctgg    1560
atgtggcaga tggggaggcg gctggcctgt cctgtcgggt gaagcacagc agtttagagg    1620
gccaggacat catcctctac tggagaaacc ccacctccga acaaaaactc atctcagaag    1680
aggatctgaa tgctgtgggc caggacacgc aggaggtcat cgtggtgcca cactccttgc    1740
cctttaaggt ggtggtgatc tcagccatcc tggccctggt ggtgctcacc atcatctccc    1800
ttatcatcct catcatgctt tggcagaaga gccacgttac ggctagaggg cccgtttaaa    1860
cccgctgatc agcctcgact gtgccttcta gttgccagcc atctgttgtt tgcccctccc    1920
ccgtgccttc cttgaccctg gaaggtgcca ctcccactgt cctttcctaa taaaatgagg    1980
aaattgcatc gcattgtctg agtaggtgtc attctattct ggggggtggg gtggggcagg    2040
acagcaaggg ggaggattgg gaagacaata gcaggcatgc tggggatgcg gtgggctcta    2100
tggcttctga ggcggaaaga accagctggg gctctagggg gtatcccac gcgccctgta     2160 gcggcgcatt aagcgcggcg ggtgtggtgg ttacgcgcag cgtgaccgct acacttgcca    2220
gcgccctagc gcccgctcct ttcgctttct cccttcctt tctcgccacg ttcgccggct     2280
ttccccgtca gctctaaat cggggcatcc ctttagggtt ccgatttagt gctttacggc     2340
```

```
acctcgaccc caaaaaactt gattagggtg atggttcacg tagtgggcca tcgccctgat    2400
agacggtttt tcgcccttg acgttggagt ccacgttctt taatagtgga ctcttgttcc    2460
aaactggaac aacactcaac cctatctcgg tctattcttt tgatttataa gggattttgg    2520
ggatttcggc ctattggtta aaaatgagc tgatttaaca aaaatttaac gcgaattaat    2580
tctgtggaat gtgtgtcagt tagggtgtgg aaagtcccca ggctcccag gcaggcagaa    2640 gtatgcaaag catgcatctc aattagtcag caaccaggtg tggaaagtcc ccaggctccc    2700
cagcaggcag aagtatgcaa agcatgcatc tcaattagtc agcaaccata gtcccgcccc    2760
taactccgcc catcccgccc ctaactccgc ccagttccgc ccattctccg ccccatggct    2820
gactaatttt ttttatttat gcagaggccg aggccgcctc tgcctctgag ctattccaga    2880
agtagtgagg aggcttttt ggaggcctag gcttttgcaa aaagctcccg ggagcttgta    2940
tatccatttt cggatctgat cagcacgtga tgaaaaagcc tgaactcacc gcgacgtctg    3000
tcgagaagtt tctgatcgaa aagttcgaca gcgtctccga cctgatgcag ctctcggagg    3060
gcgaagaatc tcgtgctttc agcttcgatg taggagggcg tggatatgtc ctgcgggtaa    3120
atagctgcgc cgatggtttc tacaaagatc gttatgttta cggcacttt gcatcggccg    3180 cgctcccgat tccggaagtg cttgacattg ggaattcag cgagagcctg acctattgca    3240
tctcccgccg tgcacagggt gtcacgttgc aagacctgcc tgaaaccgaa ctgcccgctg    3300
ttctgcagcc ggtcgcggag gccatggatg cgatcgctgc ggccgatctt agccagacga    3360
gcgggttcgg cccattcgga ccgcaaggaa tcggtcaata cactacatgg cgtgatttca    3420
tatgcgcgat tgctgatccc catgtgtatc actggcaaac tgtgatggac gacaccgtca    3480
gtgcgtccgt cgcgcaggct ctcgatgagc tgatgctttg gccgaggac tgccccgaag    3540 tccggcacct cgtgcacgcg gatttcggct ccaacaatgt cctgacggac aatggccgca    3600
taacagcggt cattgactgg agcgaggcga tgttcgggga ttcccaatac gaggtcgcca    3660
acatcttctt ctggaggccg tggttggctt gtatggagca gcagacgcgc tacttcgagc    3720
ggaggcatcc ggagcttgca ggatcgccgc ggctccgggc gtatatgctc cgcattggtc    3780
ttgaccaact ctatcagagc ttggttgacg gcaatttcga tgatgcagct tgggcgcagg    3840
gtcgatgcga cgcaatcgtc cgatccggag ccgggactgt cgggcgtaca caaatcgccc    3900
gcagaagcgc ggccgtctgg accgatggcg tgtagaagt actcgccgat agtggaaacc    3960 gacgcccag cactcgtccg agggcaaagg aatagcacgt gctacgagat ttcgattcca    4020
ccgccgcctt ctatgaaagg ttgggcttcg gaatcgtttt ccgggacgcc ggctggatga    4080
tcctccagcg cggggatctc atgctggagt tcttcgccca ccccaacttg tttattgcag    4140
cttataatgg ttacaaataa agcaatagca tcacaaattt cacaataaa gcatttttt    4200 cactgcattc tagttgtggt ttgtccaaac tcatcaatgt atcttatcat gtctgtatac    4260
cgtcgacctc tagctagagc ttggcgtaat catggtcata gctgtttcct gtgtgaaatt    4320
gttatccgct cacaattcca cacaacatac gagccggaag cataaagtgt aaagcctggg    4380
gtgcctaatg agtgagctaa ctcacattaa ttgcgttgcg ctcactgccc gctttccagt    4440
cgggaaacct gtcgtgccag ctgcattaat gaatcggcca acgcgcgggg agaggcggtt    4500
tgcgtattgg gcgctcttcc gcttcctcgc tcactgactc gctgcgctcg gtcgttcggc    4560
tgcggcgagc ggtatcagct cactcaaagg cggtaatacg gttatccaca gaatcagggg    4620
ataacgcagg aaagaacatg tgagcaaaag gccagcaaaa ggccaggaac cgtaaaaagg    4680
```

-continued

```
ccgcgttgct ggcgtttttc cataggctcc gccccctga cgagcatcac aaaaatcgac    4740
gctcaagtca gaggtggcga acccgacag gactataaag ataccaggcg tttcccctg     4800 gaagctccct cgtgcgctct cctgttccga ccctgccgct taccggatac ctgtccgcct    4860
ttctcccttc gggaagcgtg gcgctttctc aatgctcacg ctgtaggtat ctcagttcgg    4920
tgtaggtcgt tcgctccaag ctgggctgtg tgcacgaacc cccgttcag cccgaccgct     4980 gcgccttatc cggtaactat cgtcttgagt ccaacccggt aagacacgac ttatcgccac    5040
tggcagcagc cactggtaac aggattagca gagcgaggta tgtaggcggt gctacagagt    5100
tcttgaagtg gtggcctaac tacggctaca ctagaaggac agtatttggt atctgcgctc    5160
tgctgaagcc agttaccttc ggaaaaagag ttggtagctc ttgatccggc aaacaaacca    5220
ccgctggtag cggtggtttt tttgtttgca agcagcagat tacgcgcaga aaaaaggat     5280 ctcaagaaga tcctttgatc ttttctacgg ggtctgacgc tcagtggaac gaaaactcac    5340
gttaagggat tttggtcatg agattatcaa aaaggatctt cacctagatc cttttaaatt    5400
aaaaatgaag ttttaaatca atctaaagta tatatgagta aacttggtct gacagttacc    5460
aatgcttaat cagtgaggca cctatctcag cgatctgtct atttcgttca tccatagttg    5520
cctgactccc cgtcgtgtag ataactacga tacgggaggg cttaccatct ggccccagtg    5580
ctgcaatgat accgcgagac ccacgctcac cggctccaga tttatcagca ataaaccagc    5640
cagccggaag ggccgagcgc agaagtggtc ctgcaacttt atccgcctcc atccagtcta    5700
ttaattgttg ccgggaagct agagtaagta gttcgccagt taatagtttg cgcaacgttg    5760
ttgccattgc tacaggcatc gtggtgtcac gctcgtcgtt tggtatggct tcattcagct    5820
ccggttccca acgatcaagg cgagttacat gatcccccat gttgtgcaaa aaagcggtta    5880
gctccttcgg tcctccgatc gttgtcagaa gtaagttggc cgcagtgtta tcactcatgg    5940
ttatggcagc actgcataat tctcttactg tcatgccatc cgtaagatgc ttttctgtga    6000
ctggtgagta ctcaaccaag tcattctgag aatagtgtat gcggcgaccg agttgctctt    6060
gcccggcgtc aatacgggat aataccgcgc cacatagcag aactttaaaa gtgctcatca    6120
ttggaaaacg ttcttcgggg cgaaaactct caaggatctt accgctgttg agatccagtt    6180
cgatgtaacc cactcgtgca cccaactgat cttcagcatc ttttactttc accagcgttt    6240
ctgggtgagc aaaaacagga aggcaaaatg ccgcaaaaaa gggaataagg gcgacacgga    6300
aatgttgaat actcatactc ttcctttttc aatattattg aagcatttat cagggttatt    6360
gtctcatgag cggatacata tttgaatgta tttagaaaaa taaacaaata ggggttccgc    6420
gcacatttcc ccgaaaagtg ccacctgacg tc                                 6452
```

<210> SEQ ID NO 26
<211> LENGTH: 6439
<212> TYPE: DNA
<213> ORGANISM: vector

<400> SEQUENCE: 26

```
gacggatcgg gagatcctag cgtttaaact taagataact tcgtataatg tatgctatac     60
gaagttatcc cttaattaat tcccactagt ccagtgtggt ggaattctgc agatatccag    120
cacagtggcg gccgctcgag ccaattccgc ccctctccct ccccccccc taacgttact    180 ggccgaagcc gcttggaata aggccggtgt gcgtttgtct atatgtgatt ttccaccata    240
ttgccgtctt ttggcaatgt gagggcccgg aaacctggcc ctgtcttctt gacgagcatt    300
cctaggggtc tttcccctct cgccaaagga atgcaaggtc tgttgaatgt cgtgaaggaa    360
```

-continued

```
gcagttcctc tggaagcttc ttgaagacaa acaacgtctg tagcgaccct ttgcaggcag      420
cggaaccccc cacctggcga caggtgcctc tgcggccaaa agccacgtgt ataagataca      480
cctgcaaagg cggcacaacc ccagtgccac gttgtgagtt ggatagttgt ggaaagagtc      540
aaatggctct cctcaagcgt attcaacaag gggctgaagg atgcccagaa ggtaccccat      600
tgtatgggat ctgatctggg gcctcggtgc acatgcttta catgtgttta gtcgaggtta      660
aaaaaacgtc taggcccccc gaaccacggg gacgtggttt tcctttgaaa aacacgatga      720
taagcttgcc acaacccggt ctagaatgct gctgctgcca tttcaactgt tagctgttct      780
ctttcctggt ggtaacagtg aacatgcctt ccaggggccg acctcctttc atgttatcca      840
gacctcgtcc tttaccaata gtacctgggc acaaactcaa ggctcaggct ggttggatga      900
tttgcagatt catggctggg atagcgactc aggcactgcc atattcctga agccttggtc      960
taaaggtaac tttagtgata aggaggttgc tgagttagag gagatattcc gagtctacat     1020
ctttggattc gctcgagaag tacaagactt tgccggtgat ttccagatga aatacccctt     1080
tgagatccag ggcatagcag gctgtgagct acattctgga ggtgccatag taagcttcct     1140 gagggagct ctaggaggat tggatttcct gagtgtcaag aatgcttcat gtgtgccttc      1200
cccagaaggt ggcagcaggg cacagaaatt ctgtgcacta atcatacaat atcaaggtat     1260
catggaaact gtgagaattc tcctctatga aacctgcccc cgatatctct gggcgtcct      1320 caatgcagga aaagcagatc tgcaaagaca agtgaagcct gaggcctggc tgtccagtgg     1380
ccccagtcct ggacctggcc gtctgcagct tgtgtgccat gtctcaggat tctacccaaa     1440
gcccgtgtgg gtgatgtgga tgcggggtga gcaggagcag cagggcactc agctagggga     1500
catcctgccc aatgctaact ggacatggta tctccgagca accctggatg tggcagatgg     1560
ggaggcggct ggcctgtcct gtcgggtgaa gcacagcagt ttagagggcc aggacatcat     1620
cctctactgg agaaacccca cctccgaaca aaaactcatc tcagaagagg atctgaatgc     1680
tgtgggccag gacacgcagg aggtcatcgt ggtgccacac tccttgccct ttaaggtggt     1740
ggtgatctca gccatcctgg ccctggtggt gctcaccatc atctccctta tcatcctcat     1800
catgctttgg cagaagaagc cacgttaggc tagagggccc gttaaaccc gctgatcagc     1860 ctcgactgtg ccttctagtt gccagccatc tgttgtttgc cctcccccg tgccttcctt      1920 gaccctggaa ggtgccactc ccactgtcct ttcctaataa aatgaggaaa ttgcatcgca     1980
ttgtctgagt aggtgtcatt ctattctggg gggtggggtg gggcaggaca gcaagggga      2040 ggattgggaa gacaatagca ggcatgctgg ggatgcggtg ggctctatgg cttctgaggc     2100
ggaaagaacc agctggggct ctaggggta tccccacgcg ccctgtagcg cgcattaag      2160 cgcggcgggt gtggtggtta cgcgcagcgt gaccgctaca cttgccagcg ccctagcgcc     2220
cgctcctttc gctttcttcc cttcctttct cgccacgttc gccggctttc cccgtcaagc     2280
tctaaatcgg ggcatccctt tagggttccg atttagtgct ttacggcacc tcgaccccaa     2340
aaaacttgat tagggtgatg gttcacgtag tgggccatcg ccctgataga cggttttcg     2400 cccctttgacg ttggagtcca cgttctttaa tagtggactc ttgttccaaa ctggaacaac     2460
actcaaccct atctcggtct attcttttga tttataaggg attttgggga tttcggccta     2520
ttggttaaaa aatgagctga tttaacaaaa atttaacgcg aattaattct gtggaatgtg     2580
tgtcagttag ggtgtggaaa gtccccaggc tccccaggca ggcagaagta tgcaaagcat     2640
gcatctcaat tagtcagcaa ccaggtgtgg aaagtcccca ggctccccag caggcagaag     2700
```

```
tatgcaaagc atgcatctca attagtcagc aaccatagtc ccgcccctaa ctccgcccat      2760 cccgcccta  actccgccca gttccgccca ttctccgccc catggctgac taatttttt       2820 tatttatgca gaggccgagg ccgcctctgc ctctgagcta ttccagaagt agtgaggagg      2880
cttttttgga ggcctaggct tttgcaaaaa gctcccggga gcttgtatat ccatttttcgg    2940 atctgatcag cacgtgatga aaaagcctga actcaccgcg acgtctgtcg agaagtttct     3000
gatcgaaaag ttcgacagcg tctccgacct gatgcagctc tcggagggcg aagaatctcg     3060
tgctttcagc ttcgatgtag gagggcgtgg atatgtcctg cgggtaaata gctgcgccga    3120
tggtttctac aaagatcgtt atgtttatcg gcactttgca tcggccgcgc tcccgattcc    3180
ggaagtgctt gacattgggg aattcagcga gagcctgacc tattgcatct cccgccgtgc    3240
acagggtgtc acgttgcaag acctgcctga aaccgaactg cccgctgttc tgcagccggt    3300
cgcggaggcc atggatgcga tcgctgcggc cgatcttagc cagacgagcg ggttcggccc    3360
attcggaccg caaggaatcg gtcaatacac tacatggcgt gatttcatat gcgcgattgc    3420
tgatccccat gtgtatcact ggcaaactgt gatggacgac accgtcagtg cgtccgtcgc    3480
gcaggctctc gatgagctga tgctttgggc cgaggactgc cccgaagtcc ggcacctcgt    3540
gcacgcggat ttcggctcca acaatgtcct gacggacaat ggccgcataa cagcggtcat    3600
tgactggagc gaggcgatgt cggggattc  ccaatacgag gtcgccaaca tcttcttctg    3660
gaggccgtgg ttggcttgta tggagcagca gacgcgctac ttcgagcgga ggcatccgga    3720
gcttgcagga tcgccgcggc tccgggcgta tatgctccgc attggtcttg accaactcta    3780
tcagagcttg gttgacggca atttcgatga tgcagcttgg gcgcagggtc gatgcgacgc    3840
aatcgtccga tccggagccg ggactgtcgg gcgtacacaa atcgcccgca gaagcgcggc    3900
cgtctggacc gatggctgtg tagaagtact cgccgatagt ggaaaccgac gccccagcac    3960
tcgtccgagg gcaaaggaat agcacgtgct acgagatttc gattccaccg ccgccttcta    4020
tgaaaggttg ggcttcggaa tcgttttccg gacgccggc  tggatgatcc tccagcgcgg    4080
ggatctcatg ctggagttct tcgcccaccc caacttgttt attgcagctt ataatggtta    4140
caaataaagc aatagcatca caaatttcac aaataaagca tttttttcac tgcattctag    4200
ttgtggtttg tccaaactca tcaatgtatc ttatcatgtc tgtataccgt cgacctctag    4260
ctagagcttg gcgtaatcat ggtcatagct gtttcctgtg tgaaattgtt atccgctcac    4320
aattccacac aacatacgag ccggaagcat aaagtgtaaa gcctggggtg cctaatgagt    4380
gagctaactc acattaattg cgttgcgctc actgcccgct ttccagtcgg gaaacctgtc    4440
gtgccagctg cattaatgaa tcggccaacg cgcggggaga ggcggtttgc gtattgggcg    4500
ctcttccgct tcctcgctca ctgactcgct gcgctcggtc gttcggctgc ggcgagcggt    4560
atcagctcac tcaaaggcgg taatacggtt atccacagaa tcaggggata acgcaggaaa    4620
gaacatgtga gcaaaaggcc agcaaaaggc caggaaccgt aaaaaggccg cgttgctggc    4680
gtttttccat aggctccgcc cccctgacga gcatcacaaa aatcgacgct caagtcagag    4740
gtggcgaaac ccgacaggac tataaagata ccaggcgttt ccccctggaa gctccctcgt    4800
gcgctctcct gttccgaccc tgccgcttac cggatacctg tccgcctttc tcccttcggg    4860
aagcgtggcg ctttctcaat gctcacgctg taggtatctc agttcggtgt aggtcgttcg    4920
ctccaagctg ggctgtgtgc acgaaccccc cgttcagccc gaccgctgcg ccttatccgg    4980
taactatcgt cttgagtcca acccggtaag acacgactta tcgccactgg cagcagccac    5040
tggtaacagg attagcagag cgaggtatgt aggcggtgct acagagttct tgaagtggtg    5100
```

```
gcctaactac ggctacacta gaaggacagt atttggtatc tgcgctctgc tgaagccagt    5160
taccttcgga aaaagagttg gtagctcttg atccggcaaa caaaccaccg ctggtagcgg    5220
tggttttttt gtttgcaagc agcagattac gcgcagaaaa aaaggatctc aagaagatcc    5280
tttgatcttt tctacggggt ctgacgctca gtggaacgaa aactcacgtt aagggatttt    5340
ggtcatgaga ttatcaaaaa ggatcttcac ctagatcctt taaattaaa aatgaagttt     5400 taaatcaatc taaagtatat atgagtaaac ttggtctgac agttaccaat gcttaatcag    5460
tgaggcacct atctcagcga tctgtctatt tcgttcatcc atagttgcct gactccccgt    5520
cgtgtagata actacgatac gggagggctt accatctggc cccagtgctg caatgatacc    5580
gcgagaccca cgctcaccgg ctccagattt atcagcaata accagccag ccggaagggc     5640 cgagcgcaga gtggtcctg caactttatc cgcctccatc cagtctatta attgttgccg     5700
ggaagctaga gtaagtagtt cgccagttaa tagtttgcgc aacgttgttg ccattgctac    5760
aggcatcgtg gtgtcacgct cgtcgtttgg tatggcttca ttcagctccg gttcccaacg    5820
atcaaggcga gttacatgat cccccatgtt gtgcaaaaaa gcggttagct ccttcggtcc    5880
tccgatcgtt gtcagaagta agttggccgc agtgttatca ctcatggtta tggcagcact    5940
gcataattct cttactgtca tgccatccgt aagatgcttt tctgtgactg gtgagtactc    6000
aaccaagtca ttctgagaat agtgtatgcg gcgaccgagt tgctcttgcc cggcgtcaat    6060
acgggataat accgcgccac atagcagaac tttaaaagtg ctcatcattg gaaaacgttc    6120
ttcggggcga aaactctcaa ggatcttacc gctgttgaga tccagttcga tgtaacccac    6180
tcgtgcaccc aactgatctt cagcatcttt tactttcacc agcgtttctg ggtgagcaaa    6240
aacaggaagg caaaatgccg caaaaaaggg aataagggcg acacggaaat gttgaatact    6300
catactcttc ctttttcaat attattgaag catttatcag ggttattgtc tcatgagcgg    6360
atacatattt gaatgtattt agaaaaataa acaaataggg gttccgcgca catttccccg    6420
aaaagtgcca cctgacgtc                                                6439
```

<210> SEQ ID NO 27
<211> LENGTH: 7573
<212> TYPE: DNA
<213> ORGANISM: vector

<400> SEQUENCE: 27

```
agatctcggc cgcatattaa gtgcattgtt ctcgataccg ctaagtgcat tgttctcgtt      60
agctcgatgg acaagtgcat tgttctcttg ctgaaagctc gatggacaag tgcattgttc    120
tcttgctgaa agctcgatgg acaagtgcat tgttctcttg ctgaaagctc agtacccggg    180
agtaccctcg accgccggag tataaataga ggcgcttcgt ctacggagcg acaattcaat    240
tcaaacaagc aaagtgaaca cgtcgctaag cgaaagctaa gcaaataaac aagcgcagct    300
gaacaagcta acaatctgca gtaaagtgca agttaaagt gaatcaatta aaagtaacca     360
gcaaccaagt aaatcaactg caactactga aatctgccaa gaagtaatta ttgaatacaa    420
gaagagaact ctgaatactt tcaacaagtt accgagaaag aagaactcac acacagctag    480
cgaagttcct attccgaagt tcctattctc tagaaagtat aggaacttct taagataact    540
tcgtataatg tatgctatac gaagttatcc cttaattaat tcccactagt ccagtgtggt    600
ggaattctgc agatatccag cacagtggcg gccgctcgag ccaattccgc ccctctccct    660
cccccccccc taacgttact ggccgaagcc gcttggaata aggccggtgt gcgtttgtct    720
```

-continued

| | |
|---|---|
| atatgtgatt ttccaccata ttgccgtctt ttggcaatgt gagggcccgg aaacctggcc | 780 |
| ctgtcttctt gacgagcatt cctagggtc tttcccctct cgccaaagga atgcaaggtc | 840 |
| tgttgaatgt cgtgaaggaa gcagttcctc tggaagcttc ttgaagacaa acaacgtctg | 900 |
| tagcgaccct ttgcaggcag cggaaccccc cacctggcga caggtgcctc tgcggccaaa | 960 |
| agccacgtgt ataagataca cctgcaaagg cggcacaacc ccagtgccac gttgtgagtt | 1020 |
| ggatagttgt ggaaagagtc aaatggctct cctcaagcgt attcaacaag gggctgaagg | 1080 |
| atgcccagaa ggtaccccat tgtatgggat ctgatctggg gcctcggtgc acatgcttta | 1140 |
| catgtgttta gtcgaggtta aaaaacgtc taggccccc gaaccacggg acgtggttt | 1200 |
| tcctttgaaa aacacgatga taagcttgcc acaacccgt ctagcccggg ctcgagatct | 1260 |
| gcgatctaag taagcttcga atcgcgaatt cgcccaccat gctgctgctg ctgctgctgc | 1320 |
| tgggcctgag gctacagctc tccctgggca tcatcccagt tgaggaggag aacccggact | 1380 |
| tctggaaccg cgaggcagcc gaggccctgg gtgccgccaa aagctgcag cctgcacaga | 1440 |
| cagccgccaa gaacctcatc atcttcctgg gcgatgggat ggggtgtct acggtgacag | 1500 |
| ctgccaggat cctaaaaggg cagaagaagg acaaactggg gcctgagata ccctggcca | 1560 |
| tggaccgctt cccatatgtg gctctgtcca agacatacaa tgtagacaaa catgtgccag | 1620 |
| acagtggagc cacagccacg gcctacctgt gcggggtcaa gggcaacttc cagaccattg | 1680 |
| gcttgagtgc agccgcccgc tttaaccagt gcaacacgac acgcggcaac gaggtcatct | 1740 |
| ccgtgatgaa tcgggccaag aaagcaggga gtcagtgggg agtggtaacc accacacgag | 1800 |
| tgcagcacgc ctcgccagcc ggcacctacg cccacgggt gaaccgcaac tggtactcgg | 1860 |
| acgccgacgt gcctgcctcg gcccgccagg aggggtgcca ggacatcgct acgcagctca | 1920 |
| tctccaacat ggacattgac gtgatcctag gtggaggccg aaagtacatg tttcgcatgg | 1980 |
| gaaccccaga ccctgagtac ccagatgact acagccaagg tgggaccagg ctggacggga | 2040 |
| agaatctggt gcaggaatgg ctggcgaagc gccagggtgc ccggtatgtg tggaaccgca | 2100 |
| ctgagctcat gcaggcttcc ctggaccgt ctgtgaccca tctcatgggt ctctttgagc | 2160 |
| ctggagacat gaaatacgag atccaccgag actccacact ggacccctcc ctgatggaga | 2220 |
| tgacagaggc tgccctgcgc ctgctgagca ggaaccccg cggcttcttc ctcttcgtgg | 2280 |
| agggtggtcg catcgaccat ggtcatcatg aaagcagggc ttaccgggca ctgactgaga | 2340 |
| cgatcatgtt cgacgacgcc attgagaggg cgggccagct caccagcgag gaggacacgc | 2400 |
| tgagcctcgt cactgccgac cactcccacg tcttctcctt cggaggctac cccctgcgag | 2460 |
| ggagctccat cttcgggctg gcccctggca aggcccggga caggaaggcc tacacggtcc | 2520 |
| tcctatacgg aaacggtcca ggctatgtgc tcaaggacgg cgcccggccg gatgttaccg | 2580 |
| agagcgagag cgggagcccc gagtatcggc agcagtcagc agtgccctg gacgaagaga | 2640 |
| cccacgcagg cgaggacgtg gcggtgttcg cgcgcggccc gcaggcgcac ctggttcacg | 2700 |
| gcgtgcagga gcagaccttc atagcgcacg tcatggcctt cgccgcctgc ctggagccct | 2760 |
| acaccgcctg cgacctggcg ccccccgccg gcaccaccga cgccgcgcac ccgggttact | 2820 |
| ctagagtcgg gcggccggc cgcttcgagc agacatctcc cgggaatccg cggctgcagg | 2880 |
| tcgacgaaca aaaactcatc tcagaagagg atctgaatgc tgtgggccag acacgcagg | 2940 |
| aggtcatcgt ggtgccacac tccttgccct ttaaggtggt ggtgatctca gccatcctgg | 3000 |
| ccctggtggt gctcaccatc atctccctta tcatcctcat catgctttgg cagaagaagc | 3060 |
| cacgttaggc ggccgctcga gatcagctag agggcccgtt taaacccgct gatcagcctc | 3120 |

```
gactgtgcct tctagttgcc agccatctgt tgtttgcccc tccccgtgc cttccttgac      3180 cctggaaggt gccactccca ctgtcctttc ctaataaaat gaggaaattg catcgcattg      3240
tctgagtagg tgtcattcta ttctgggggg tggggtgggg caggacagca aggggggagga    3300 ttgggaagac aatagcaggc atgctgggga tgcggtgggc tctatggctt ctgaggcgga     3360
aagaaccagc tggggctcta gggggtatcc ccacgcgccc tgtagcggcg cattaagcgc     3420
ggcgggtgtg gtggttacgc gcagcgtgac cgctacactt gccagcgccc tagcgcccgc     3480
tcctttcgct ttcttccctt cctttctcgc cacgttcgcc ggctttcccc gtcaagctct     3540 aaatcgggc atccctttag ggttccgatt tagtgcttta cggcacctcg accccaaaaa     3600
acttgattag ggtgatggtt cacgtagtgg gccatcgccc tgatagacgg ttttttcgccc    3660 tttgacgttg gagtccacgt tctttaatag tggactcttg ttccaaactg gaacaacact     3720
caaccctatc tcggtctatt cttttgattt ataaggggatt ttgggggatttt cggcctattg  3780 gttaaaaaat gagctgattt aacaaaaatt taacgcgaat taattctgtg aatgtgtgt      3840 cagttagggt gtgaaagtc cccaggctcc ccaggcaggc agaagtatgc aaagcatgca     3900
tctcaattag tcagcaacca ggtgtggaaa gtccccaggc tccccagcag gcagaagtat    3960
gcaaagcatg catctcaatt agtcagcaac catagtcccg cccctaactc cgcccatccc    4020
gcccctaact ccgcccagtt ccgcccattc tccgcccat ggctgactaa ttttttttat     4080
ttatgcagag gccgaggccg cctctgcctc tgagctattc cagaagtagt gaggaggctt    4140
ttttggaggc ctaggctttt gcaaaaagct cccgggagct tgtatatcca ttttcggatc    4200
tgatcaagag acaggatgag gatcgtttcg catgattgaa caagatggat tgcacgcagg    4260
ttctccggcc gcttgggtgg agaggctatt cggctatgac tgggcacaac agacaatcgg    4320
ctgctctgat gccgccgtgt tccggctgtc agcgcagggg cgcccggttc ttttttgtcaa   4380 gaccgacctg tccggtgccc tgaatgaact gcaggacgag gcagcgcggc tatcgtggct    4440
ggccacgacg ggcgttcctt gcgcagctgt gctcgacgtt gtcactgaag cgggaaggga    4500
ctggctgcta ttgggcgaag tgccggggca ggatctcctg tcatctcacc ttgctcctgc    4560
cgagaaagta tccatcatgg ctgatgcaat gcggcggctg catacgcttg atccggctac    4620
ctgcccattc gaccaccaag cgaaacatcg catcgagcga gcacgtactc ggatggaagc    4680
cggtcttgtc gatcaggatg atctggacga agagcatcag gggctcgcgc cagccgaact    4740
gttcgccagg ctcaaggcgc gcatgcccga cggcgaggat ctcgtcgtga cccatggcga    4800
tgcctgcttg ccgaatatca tggtggaaaa tggccgcttt tctggattca tcgactgtgg    4860
ccggctgggt gtggcggacc gctatcagga catagcgttg gctacccgtg atattgctga    4920
agagcttggc ggcgaatggg ctgaccgctt cctcgtgctt tacggtatcg ccgctcccga    4980
ttcgcagcgc atcgccttct atcgccttct tgacgagttc ttctgagcgg gactctgggg    5040
ttcgaaatga ccgaccaagc gacgcccaac ctgccatcac gagatttcga ttccaccgcc    5100
gccttctatg aaaggttggg cttcggaatc gttttccggg acgccggctg atgatcctc     5160 cagcgcgggg atctcatgct ggagttcttc gcccacccca acttgtttat tgcagcttat    5220
aatggttaca aataaagcaa tagcatcaca aatttcacaa ataaagcatt ttttccactg    5280
cattctagtt gtggtttgtc caaactcatc aatgtatctt atcatgtctg tacataactt    5340
cgtataatgt atgctatacg aagttattac cgtcgacctc tagctagagc ttggcgtaat    5400
catggtcata gctgtttcct gtgtgaaatt gttatccgct cacaattcca cacaacatac    5460
```

```
gagccggaag cataaagtgt aaagcctggg gtgcctaatg agtgagctaa ctcacattaa    5520
ttgcgttgcg ctcactgccc gctttccagt cgggaaacct gtcgtgccag ctgcattaat    5580
gaatcggcca acgcgcgggg agaggcggtt tgcgtattgg gcgctcttcc gcttcctcgc    5640
tcactgactc gctgcgctcg gtcgttcggc tgcggcgagc ggtatcagct cactcaaagg    5700
cggtaatacg gttatccaca gaatcagggg ataacgcagg aaagaacatg tgagcaaaag    5760
gccagcaaaa ggccaggaac cgtaaaaagg ccgcgttgct ggcgtttttc cataggctcc    5820
gcccccctga cgagcatcac aaaaatcgac gctcaagtca gaggtggcga aacccgacag    5880
gactataaag ataccaggcg tttccccctg gaagctccct cgtgcgctct cctgttccga    5940
ccctgccgct taccggatac ctgtccgcct ttctcccttc gggaagcgtg gcgctttctc    6000
aatgctcacg ctgtaggtat ctcagttcgg tgtaggtcgt tcgctccaag ctgggctgtg    6060
tgcacgaacc ccccgttcag cccgaccgct gcgccttatc cggtaactat cgtcttgagt    6120
ccaacccggt aagacacgac ttatcgccac tggcagcagc cactggtaac aggattagca    6180
gagcgaggta tgtaggcggt gctacagagt tcttgaagtg gtggcctaac tacggctaca    6240
ctagaaggac agtatttggt atctgcgctc tgctgaagcc agttaccttc ggaaaaagag    6300
ttggtagctc ttgatccggc aaacaaacca ccgctggtag cggtggtttt tttgtttgca    6360
agcagcagat tacgcgcaga aaaaaggat ctcaagaaga tcctttgatc ttttctacgg     6420
ggtctgacgc tcagtggaac gaaaactcac gttaagggat tttggtcatg agattatcaa    6480
aaaggatctt cacctagatc cttttaaatt aaaaatgaag ttttaaatca atctaaagta    6540
tatatgagta aacttggtct gacagttacc aatgcttaat cagtgaggca cctatctcag    6600
cgatctgtct atttcgttca tccatagttg cctgactccc cgtcgtgtag ataactacga    6660
tacgggaggg cttaccatct ggccccagtg ctgcaatgat accgcgagac ccacgctcac    6720
cggctccaga tttatcagca ataaaccagc cagccggaag ggccgagcgc agaagtggtc    6780
ctgcaacttt atccgcctcc atccagtcta ttaattgttg ccgggaagct agagtaagta    6840
gttcgccagt taatagtttg cgcaacgttg ttgccattgc tacaggcatc gtggtgtcac    6900
gctcgtcgtt tggtatggct tcattcagct ccggttccca acgatcaagg cgagttacat    6960
gatcccccat gttgtgcaaa aaagcggtta gctccttcgg tcctccgatc gttgtcagaa    7020
gtaagttggc cgcagtgtta tcactcatgg ttatggcagc actgcataat tctcttactg    7080
tcatgccatc cgtaagatgc ttttctgtga ctggtgagta ctcaaccaag tcattctgag    7140
aatagtgtat gcggcgaccg agttgctctt gcccggcgtc aatacgggat aataccgcgc    7200
cacatagcag aactttaaaa gtgctcatca ttggaaaacg ttcttcgggg cgaaaactct    7260
caaggatctt accgctgttg agatccagtt cgatgtaacc cactcgtgca cccaactgat    7320
cttcagcatc ttttactttc accagcgttt ctgggtgagc aaaaacagga aggcaaaatg    7380
ccgcaaaaaa gggaataagg gcgacacgga aatgttgaat actcatactc ttcctttttc    7440
aatattattg aagcatttat cagggttatt gtctcatgag cggatacata tttgaatgta    7500
tttagaaaaa taaacaaata ggggttccgc gcacatttcc ccgaaaagtg ccacctgacg    7560
tcgacggatc ggg                                                      7573
```